(12) United States Patent
Hossack et al.

(10) Patent No.: US 7,641,480 B1
(45) Date of Patent: Jan. 5, 2010

(54) AXIAL MULTI-WIRE BARREL CONNECTOR FOR INTERCONNECTING A CONTROLLER CONSOLE TO CATHETER INCLUDING A DISTALLY MOUNTED ULTRASOUND TRANSDUCER ASSEMBLY

(75) Inventors: Norman H. Hossack, Folsom, CA (US); Stephen Davies, Folsom, CA (US)

(73) Assignee: Volcano Corporation, Rancho Cordova, CA (US)

( * ) Notice: Subject to any disclaimer, the term of this patent is extended or adjusted under 35 U.S.C. 154(b) by 0 days.

(21) Appl. No.: 12/141,784

(22) Filed: Jun. 18, 2008

(51) Int. Cl.
*H01R 12/00* (2006.01)

(52) U.S. Cl. .................. 439/67; 439/335; 439/909; 439/492; 439/675

(58) Field of Classification Search ............ 439/67, 439/492, 314, 316, 318, 335, 367–369, 281, 439/675, 668, 669, 660, 909
See application file for complete search history.

(56) References Cited

U.S. PATENT DOCUMENTS

| | | | | |
|---|---|---|---|---|
| 3,871,735 A | * | 3/1975 | Herrmann, Jr. ............. | 439/585 |
| 4,440,464 A | * | 4/1984 | Spinner ..................... | 439/218 |
| 5,662,488 A | * | 9/1997 | Alden ....................... | 439/314 |
| 5,685,730 A | * | 11/1997 | Cameron et al. ............ | 439/335 |
| 6,206,714 B1 | * | 3/2001 | Bernardini ................. | 439/335 |
| 6,416,334 B1 | * | 7/2002 | Plishner .................... | 439/75 |
| 6,912,423 B2 | * | 6/2005 | Ley et al. ................... | 607/37 |
| 7,077,677 B2 | * | 7/2006 | Sanuki ...................... | 439/318 |

* cited by examiner

*Primary Examiner*—Tho D Ta
(74) *Attorney, Agent, or Firm*—Leydig, Voit & Mayer, Ltd.

(57) ABSTRACT

A connector assembly is disclosed for coupling a signal wire bundle from a controller console to a hand-operated catheter assembly. The connector includes a female connector component having a cylindrical cavity, wire fingers disposed within the cylindrical cavity, a guide peg disposed on a surface of the cylindrical cavity at a point proximate an opening of the cylindrical cavity, and a central pin disposed on a base surface at a closed end of the cylindrical cavity. The connector also includes a male connector component having a substantially cylindrical shape having a non-uniform transverse cross-section radius. The male connector component comprises a set of signal leads disposed along arcs of a cylindrical surface of the male connector, a slot defined within the male connector's surface is arranged to accept the guide peg of the female connector component and constrain the relative positions of the male connector and female connector during engagement.

14 Claims, 40 Drawing Sheets

AXIAL MULTI-WIRE BARREL CONNECTOR FOR INTERCONNECTING A CONTROLLER CONSOLE TO CATHETER INCLUDING A DISTALLY MOUNTED ULTRASOUND TRANSDUCER ASSEMBLY

FIELD OF THE INVENTION

The present invention generally relates to ultrasound catheters. More specifically, the present invention pertains to a connector assembly used to couple a bundle of wires to a corresponding signal line set for an ultrasound intracardiac echocardiography (ICE) catheter with flexed steering to transmit ultrasound and receive echoes during an intracardiac diagnostics procedure.

BACKGROUND OF THE INVENTION

Diagnostic and therapeutic ultrasound catheters have been designed for use inside many areas of the human body. In the cardiovascular system, two common diagnostic ultrasound methods are intravascular ultrasound (IVUS) and intracardiac echocardiography (ICE). Typically a single rotating transducer or an array of transducer elements is used to transmit ultrasound at the tips of the catheters. The same transducers (or separate transducers) are used to receive echoes from the tissue. A signal generated from the echoes is transferred to a console which allows for the processing, storing, display, or manipulation of the ultrasound-related data.

IVUS catheters are typically used in the large and small blood vessels (arteries or veins) of the body, and are almost always delivered over a guidewire having a flexible tip. ICE catheters are usually used to image the chambers of the heart and surrounding structures. Commercially-available ICE catheters are not designed to be delivered over a guidewire, but instead have distal ends which can be articulated by a steering mechanism located in a handle at the proximal end of the catheter. Examples of ICE catheters include ones provided by EP Medsystems (ViewFlex™ Intracardiac Ultrasound Deflectable catheter) and Siemens/ACUSON (AcuNav™ Ultrasound Catheter). Both the ViewFlex and the AcuNav catheters utilize a linear array of multiple transducer elements, e.g., 64 elements, at their tips.

The large number of signal channels present in the cables connecting an ICE catheter transducer assembly to a controller console raises substantial design challenges. Interconnecting a cable from the non-sterile field to an ICE catheter assembly handle should be accomplished using a connector assembly that, in addition to maintaining the sterile field, provides: low engagement/mating force, reliable alignment/ mating of corresponding signal leads, and a secure connection after mating. These objectives are supplemented by additional objectives such as: small size, low mass, durability (multiple mate/de-mate cycles), low cost, complete coverage/ sealing of contacting wires, and simple mating action.

SUMMARY OF THE INVENTION

A barrel connector for coupling a signal wire bundle from a controller console to a hand-operated catheter assembly is disclosed. More particularly a multi-wire barrel connector is described herein for coupling a signal wire bundle from a controller console to a hand-operated catheter assembly. The multi-wire barrel connector includes a female connector component having a cylindrical cavity. In addition the female connector component includes a set of wire fingers disposed within the cylindrical cavity. The set of wire fingers provide points of termination for a set of signal lines. The female connector component includes a guide peg disposed on a surface of the cylindrical cavity at a point proximate an opening of the cylindrical cavity. The female connector also includes a central pin disposed on a base surface at a closed end of the cylindrical cavity. The central pin extends from the base surface along a central axis of the cylindrical cavity.

The multi-wire barrel connector also includes a male connector component having a substantially cylindrical shape having a non-uniform transverse cross-section radius. The male connector component comprises a set of signal leads disposed along arcs of a cylindrical surface of the male connector. The set of signal leads are disposed along a majority of a length of the male connector component. The male connector includes a slot defined within the male connector's surface. The slot is arranged to accept the guide peg of the female connector component and constrain the relative positions of the male connector and female connector during engagement. The slot comprises at least a first segment running lengthwise along the male connector and a second segment guiding rotational engagement between the set of wire fingers and the set of signal leads. Finally, rotational lock structures incorporated into the female and male connector components ensure full engagement between the male connector and female connector component is maintained after rotating the male connector and female connector components into a fully engaged relationship.

BRIEF DESCRIPTION OF THE DRAWINGS

The various features of the present invention and the manner of attaining them will be described in greater detail with reference to the following description, claims, and drawings, wherein reference numerals appear in more than one drawing, where appropriate, to indicate a correspondence between the referenced items, and wherein:

Figure 1:
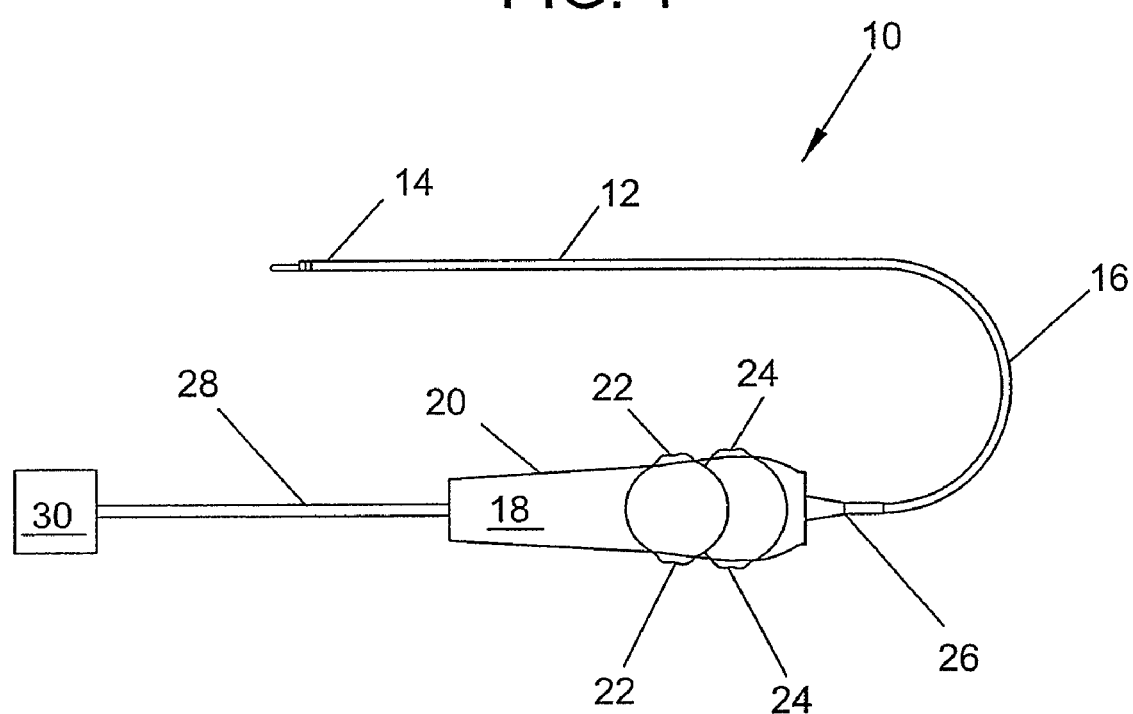
FIG. 1 is an illustration of an intracardiac echocardiography (ICE) catheter assembly including a connector.

It should be understood that the sizes of the different components in the figures may not be in proportion and are shown for visual clarity and for the purpose of explanation.

DETAILED DESCRIPTION OF THE DRAWINGS

The following embodiments are related to an ultrasound catheter assembly 10 that utilizes a barrel connector assembly wherein a set of exposed contacts on a male connector component contact a corresponding set of wire fingers carried by a female connector component's inner cylindrical surface. For purposes of illustration, the ultrasound catheter assembly 10 is described in the context of an ultrasound catheter system for use as an intracardiac echocardiography (ICE) catheter. Other applications of the disclosed catheter assembly are contemplated in alternative embodiments. The connector described herein incorporates a barrel design characterized by a substantially cylindrical space defining the complimentary male and female components of the connector joining a multi-wire (e.g., approximately 64 line) signal line set from a controller console to a corresponding signal line set for an array of (64) transducer elements. The transducer elements make up a transducer array incorporated into an ICE catheter assembly. In the illustrative example, the male component comprises a multi-piece assembly that, when placed together, form a cylindrical-shaped member. In an exemplary embodiment, a pair of flex circuits, each comprising a set of (32) signal lines deposited on a flexible substrate, are affixed to one or more pieces of the multi-piece assembly. Contacts for the signal lines of the flexible substrate are located on an outer surface of the cylindrical-shaped member of the male component.

The female connector component of the barrel connector assembly includes a complimentary cylindrical cavity. In an exemplary embodiment, a set of (64) signal leads terminate within the female component at two sets of (32) parallel wire fingers. The wire fingers are, in turn, connected to signal lines coupled to a control console signal interface. The wire fingers are trailing (dragging) in nature and exert enough force on the corresponding male contacts to ensure constant contact while the ICE catheter assembly is in operation. The wire fingers thus exert minimal force to minimize wear on a re-usable portion of the connector components. In an exemplary embodiment the re-usable connector component is the female component. In alternative embodiments the male component is the reused component of the barrel connector assembly.

Guides are built into the male and female components to ensure proper engagement of male component contacts and corresponding ones of the wire fingers when the male component is inserted into and then rotated within the female component. In the exemplary embodiment a guide pin extends from a bottom of the female component's cylindrical cavity. The guide pin enters an axial shaft within the male component. The guide pin operates as a pivot point during rotation of the male component and female component to affect an electrically conductive connection between the contacts and corresponding wire fingers.

The 64 exposed contacts of the male component engage the corresponding ones of the 64 wire fingers of the female component when the male component is inserted into and then rotated only a small amount, less than a quarter turn, within the female component. Proper alignment of the male component's contacts and the female component's wire fingers is facilitated, in an illustrative embodiment, by a combination of a guide peg and corresponding channel/slot. The peg matches a side opening in the corresponding channel/slot. When the male component is initially inserted, the channel guides the peg to ensure that the wire fingers of the female component are not damaged during insertion. When the male component has been inserted to a proper depth in the female component, a second portion of the channel, running along an arc of the outer cylindrical surface of the male component, guides the peg to ensure the contacts and the wire fingers are properly aligned as the male and female components are rotated toward a fully engaged position. The male and female components are described further herein below with reference to, for example, FIGS. 27, 28a, 28b, and 29, after first describing an exemplary ICE catheter assembly with which the above-described connector is advantageously used.

FIG. 1 illustratively depicts an embodiment of the catheter assembly 10 including a catheter shaft 12. The catheter shaft 12 is a generally flexible elongate member having a distal segment 14, a proximal segment 16, and at least one lumen (not shown). The proximal segment 16 is attached to a handle 18. The handle 18 includes, by way of example, a housing 20, a first in-line steering actuator 22 (e.g., a knob), and a second steering actuator 24.

The first and second actuators 22 and 24 are manipulated by a user moving an exposed control surface of the actuators 22 and 24 (using a finger/thumb) lengthwise along the length of the housing 20 of the handle 18 (as opposed to across the width of the handle 18). As used herein the term "lengthwise along the housing" includes the arrangement depicted in the exemplary embodiments (e.g., FIGS. 18, 19 and 25) as well as other arrangements where the movement of an exposed control surface of the actuators is primarily along the lengthwise axis of the handle 18 (e.g., tilted by 30 degrees). "Exposed control surface" refers to a portion of the actuators 22 and 24 that is physically accessible to a user's finger/thumb through, for example, an opening in the housing 20. Furthermore, a variety of actuator mechanisms are envisioned for actuators 22 and 24 in alternative embodiments. In the illustrative embodiment, the first actuator 22 and second actuator 24 comprise rotatable knobs that rotate on an axis that is transverse to the lengthwise axis of the handle 18 when a user moves a thumb along the handle 18's length. In alternative embodiments, thumb-controlled slider actuators replace the rotating knobs.

The distal segment 14 is, by way of example, 10 cm long. However, an exemplary range for the length of the distal segment 14 is from 5 cm to 20 cm. A tip of the distal segment 14 has a generally smaller diameter than the diameter of the proximal segment 16 of the catheter shaft. The catheter shaft 12 is made, by way of example, of engineered nylon (such as Pebax® polyether block amide) and includes a tube or tubing, alternatively called a catheter tube or catheter tubing that has at least one lumen.

In the illustrative example in FIG. 1, the first and second steering actuators 22 and 24 are accessible (have exposed control surfaces through the housing 20) on two sides of the handle 18. A potential advantage of the depicted arrangement of the steering actuators 22 and 24 is the ability of a user to control the actuators 22 and 24 with a same hand that is holding the handle 18. A strain relief 26 protects the catheter shaft 12 at a point where the catheter shaft proximal segment 16 meets the handle 18. A cable 28 connects the handle 18 to a connector 30. The connector 30, which can be any of many possible configurations, is configured to interconnect with an ultrasound system for processing, storing, manipulating, and displaying data obtained from signals generated by a sensor mounted at the distal segment 14 of the catheter shaft 12.

Figure 2:
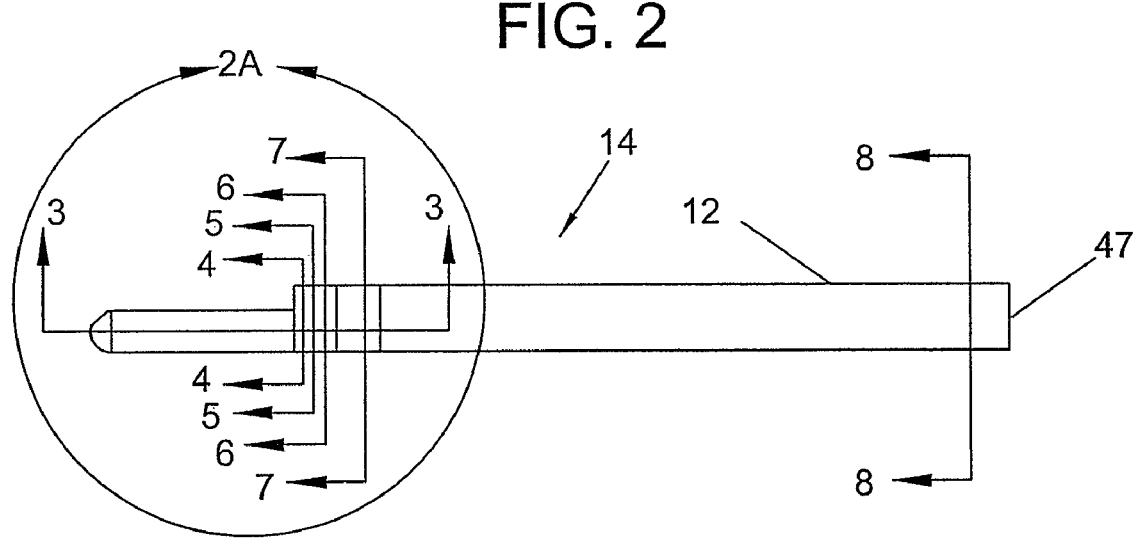
FIG. 2 is an illustration of the distal end of the ICE catheter.
Figure 2A:
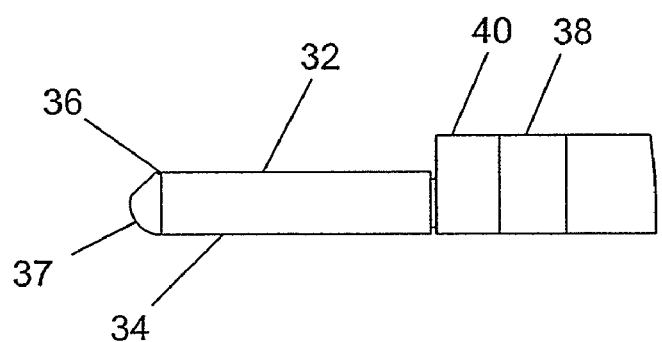
FIG. 2A is a detail view of the distal end of the ICE catheter.

FIGS. 2, 2A, 2B, and 8 illustrate a first embodiment of an ultrasound catheter 10 incorporating a handle and knob-based actuator control mechanism that supports single-handed position manipulation/control by a user of a sensor mounted at the distal segment 14 of the catheter shaft 12. Turning to FIGS. 2 and 2A, the distal segment 14 of the catheter shaft 12 includes a rotatable tip 34 that extends from the distal segment 14 and rotates relative to an axis of the catheter shaft 12. The catheter shaft 12 has a lumen 47 as illustrated more clearly in FIGS. 7 and 8.

In the illustrative embodiment depicted in FIGS. 2 and 2A the rotatable tip 34 comprises a transducer probe assembly including transducers and a flex circuit. By way of example, the rotatable tip 34 comprises a linearly arranged transducer array 32 including a set of transducer elements that are rectangular in shape, and the transducer probe assembly generally has a diameter that is smaller than the diameter of the distal segment 14 of the catheter shaft 12. Furthermore rotatable tip 34 connects to a distal segment of the catheter 10 with a rotatably smooth sliding contact. The rotatable tip 34 includes a backing material 36. The rotatable tip 34 also includes a rounded tip portion 37 (atraumatic) to reduce the incidence of trauma to the human body as the tip 34 is fed into a patient. The rounded tip portion 37 is made from material such as a room temperature vulcanizing (RTV) elastomer or any silicone rubber. The transducer array 32 is isolated from bodily fluids by the same materials as utilized in the rounded tip portion 37.

The rotatable tip 34 is potentially rotatable by manual or motorized means. The rotatable tip 34 can be adapted to rotate in a variety of angular rotational ranges. For example, in one embodiment the tip 34 is rotated bidirectionally in a 360° field of view. Alternatively the tip 34 rotation is restricted to rotate bidirectionally in a limited rotational range, e.g., clockwise or counter-clockwise by 180° in each direction. In a first embodiment, the rotating tip 34 is rotated by manipulation of the first in-line steering actuator 22 of the handle 18, and is capable of approximately 180° of rotation in the clockwise direction and 180° rotation in the counter-clockwise direction.

Figure 2B:
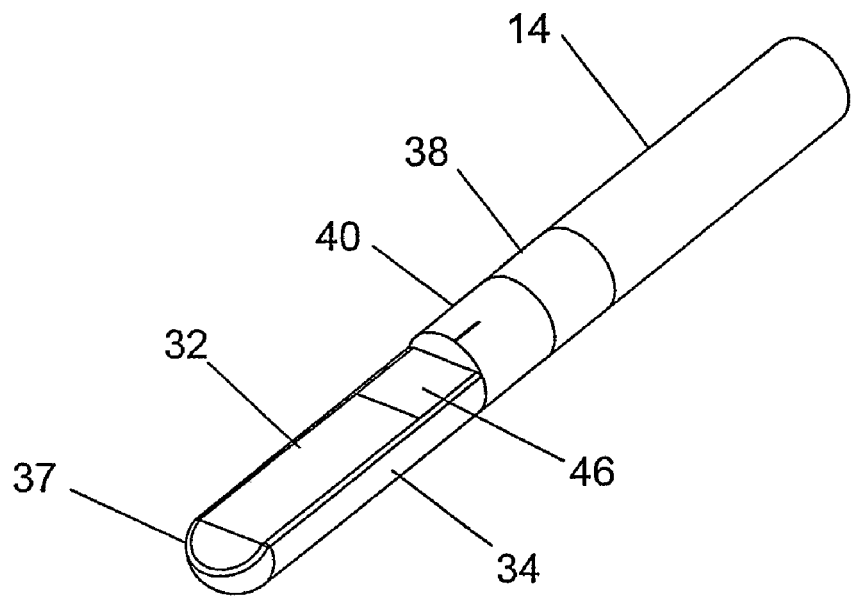
FIGS. 2B and 2C are illustrations of rotational steering mode of an ICE catheter.
Figure 2C:
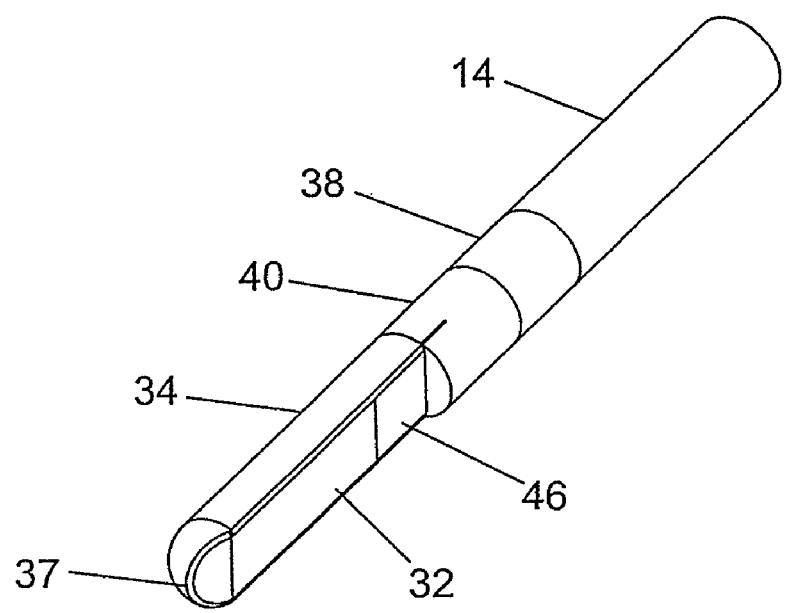

FIGS. 2B and 2C illustrate rotational steering affected by the actuator 22 of the catheter assembly 10. FIG. 2B illustrates the distal segment 14 in a central, neutral, or intermediate/relaxed position in between the two extremes of tip 34's rotation in relation to a distal segment termination 40 of the catheter shaft 12. In order to rotationally steer the transducer array 32 to the rotated position illustrated in FIG. 2C, the first steering actuator 22, a rotating knob, is turned in a first rotational direction with respect to the relatively fixed position of the handle 18. The disclosed rotational steering mechanism facilitates smooth panning movement and pinpoint accuracy in imaging the desired tissue with the transducer array 32. To rotate the catheter tip 34 in the opposite direction (e.g., counter-clockwise), the first steering actuator 22 (e.g., rotating knob) is moved in an opposing second rotational direction with respect to the handle 18.

In the illustrative embodiment depicted in FIG. 2A, the exemplary transducer array 32 is a linear array of 64 transducer elements that are individually controlled to fire and sense echoes in phases, but can alternatively be any number of transducer elements, for example 16, 32, 128 or 256. Alternatively the transducer array can be a curved array. In addition, the array can be a two-dimensional array, for example, two rows of 16 elements or four rows of 16 elements.

The transducer array illustrated in this embodiment is coupled to a single multiplexer chip 46 controlling the transmission/reception of signals to/from the array 32. In an exemplary embodiment a multiplexer effectively reduces the number of wires passing through the majority of the length of the catheter shaft 12 by one half the transducer signal wires; for example, processing the signals received on 64 transducer elements with 32 electrical conduits instead of 64. In yet other exemplary multiplexers, further reduction is achieved by a factor of four, eight, or more. Whereas commercially-available intracardiac echocardiography catheter shafts are typically 8 French to 10 French in diameter, the multiplexing in the present system provides for a catheter shaft that is 6 French or smaller in diameter. This results in a less invasive procedure and less trauma to the patient. As a result of the smaller diameter of the catheter shaft of the present system, the size of the puncture in the access artery or vein (e.g., femoral vein, femoral artery, subclavian vein, jugular vein) is smaller, allowing for faster healing, fewer complications, more space for other catheters and an ability to perform procedures in smaller patients such as pediatric patients.

Though the single multiplexer chip 46 is illustrated in FIGS. 2B and 2C, more multiplexers can be used.

Also, the (reduction) ratio between transducer elements and wires can be increased to further reduce the number of wires within the catheter shaft 12, and thus reduce the catheter diameter. Alternatively, multiplexers are used to increase the number of transducer elements on an 8 F to 10 F catheter for greater than 64 transducer elements using 64 electrical wires. Each transducer directly connects to an electrical conductor/wire on a flex circuit before the multiplexer. For example a 256 element transducer array can be configured as a 1×256 linear array, a 2×128 1.5D array or alternatively as a 16×16 array for 3D imaging. A catheter with an array configured for 3D or three-dimensional imaging has the ability to be used in 3D applications, for example to guide a "smart" ablation or other therapeutic procedure to a specific point or area in a 3D map. By placing in the tip 34 a tracking device such as a wire loop or RF antenna for determining, positioning, and tracking the position and orientation of the catheter tip, a three dimensional map or image of the entire area of study can be obtained. The coordinates of the catheter tip 34 are downloaded and combined with multiple "slices" or frames of ultrasound image data.

Figure 2D:
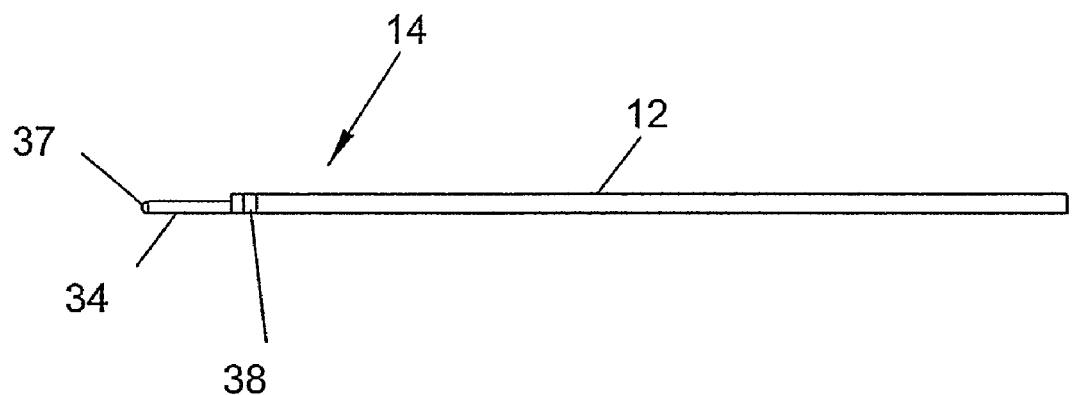
FIGS. 2D and 2E are illustrations of a flexing steering mode of an ICE catheter.
Figure 2E:
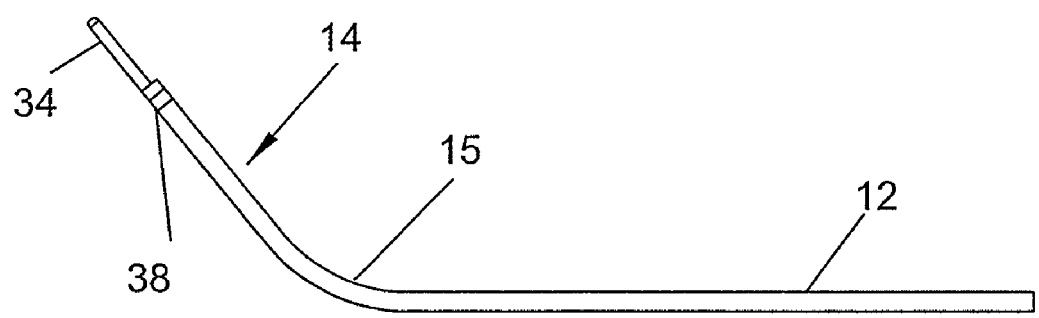

FIGS. 2D and 2E illustrate distal segment 14 flexing steering affected by the second actuator 24 in the first embodiment. The catheter 12 is flexed, using the actuator 24, from a straight configuration as illustrated in FIG. 2D into a flexed steering configuration, as illustrated in FIG. 2E. In addition, the catheter 12's distal segment 14 is steerable into any number of flexed positions in between the straight configuration of FIG. 2D and the flexed configuration of FIG. 2E, and can even be flexed beyond the configuration of FIG. 2E. The catheter is capable of flexing past the 90° point in each direction and has an angular range of 0° to 150° from the straight or neutral configuration. The second direction is similar to what has been illustrated in FIG. 2E, and it can be appreciated that it is simply the mirror image of the configuration of FIG. 2E illustrated for the first direction.

To affect flexing the distal segment 14 in the manner described above, the second steering actuator 24 (e.g., knob) is turned in a first rotational direction with respect to the relatively fixed position handle 18. Rotating the actuator 24 in the first direction causes a first steering wire 56 (see, e.g., FIG. 8) to apply tension to a steering bulkhead 38 forcing the distal segment 14 of the catheter shaft 12 to bend at bending joint 15 (see, FIG. 2E). In order to flex the catheter in the opposite direction, the second steering actuator 24 is turned in an opposing second rotational direction with respect to the handle 18. This causes second steering wire 58 to apply tension to an opposite side of steering bulkhead 38, forcing the catheter to bend in an opposite direction at the bending joint 15. The catheter assembly 10, by way of example, supports bidirectional flexed steering by at least 150 degrees in each direction from a neutral or straight catheter position. Using the combination of these two steering modes (rotational and flexing) is much more intuitive to the user than a steering mechanism based solely on either rotation or flexing—but not both. In an example of a method for using the catheter assembly 10 having both rotational and flex steering, the catheter tip 34 is first placed into a desired location of the body, for example the right atrium of the heart. While visualizing the catheter tip position 34, such as with ultrasound or fluoroscopy, the second steering actuator 24 is adjusted until the catheter orientation is close to the desired orientation. The first steering actuator 22 is then adjusted so that the rotatable tip 34 points the transducer array 32 in the desired orientation for the target image plane.

Figure 9:
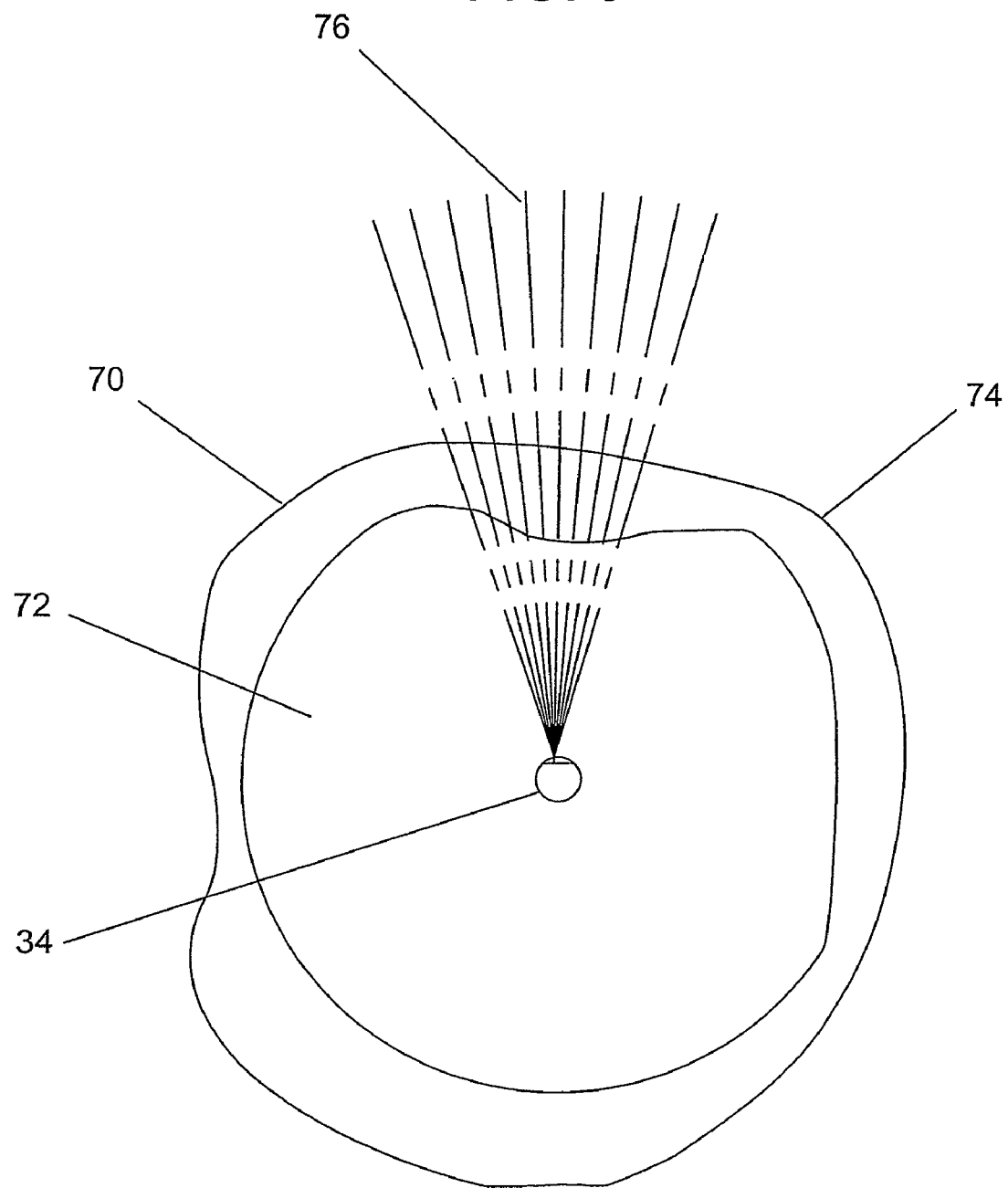
FIGS. 9 and 10 illustrate a rotational steering catheter being used to image structures in the heart.
Figure 10:
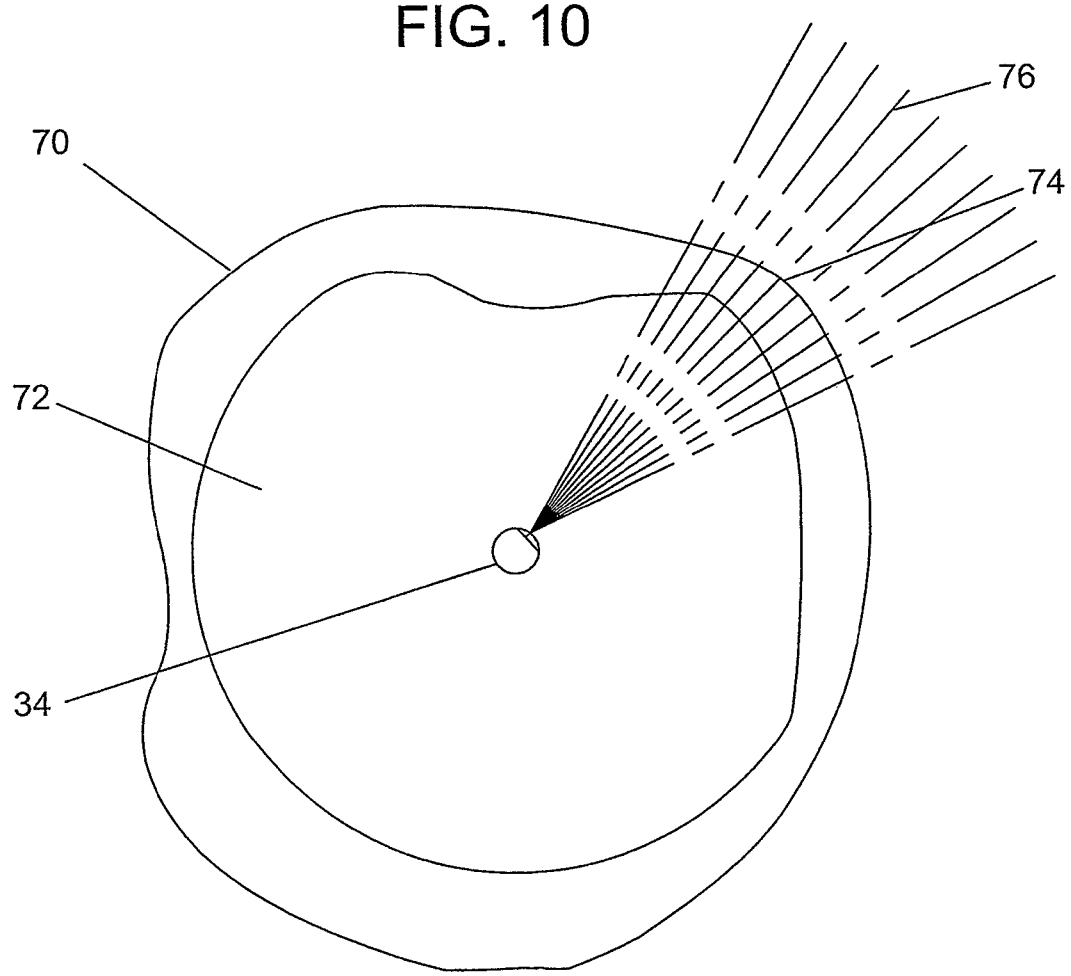

FIG. 9 illustrates the rotatable catheter tip 34 in place in a right atrium 72 of the heart. Second steering actuator 24 has already been adjusted to orient the catheter tip 34 in the correct tip flex position. As illustrated in FIG. 9 the desired structure to be imaged, an atrial septum 74, is not being imaged by ultrasound waves 76. A heart wall 70 is instead being imaged. By manipulating first steering actuator 22, the rotatable tip 34 is turned so that the ultrasound 76 impinges on the desired structure. This is done without torquing/twisting the catheter shaft 12. In FIG. 10, the adjustment of first steering actuator 22 is complete, and the rotatable tip 34 is now in position to image the atrial septum 74.

Figure 18:
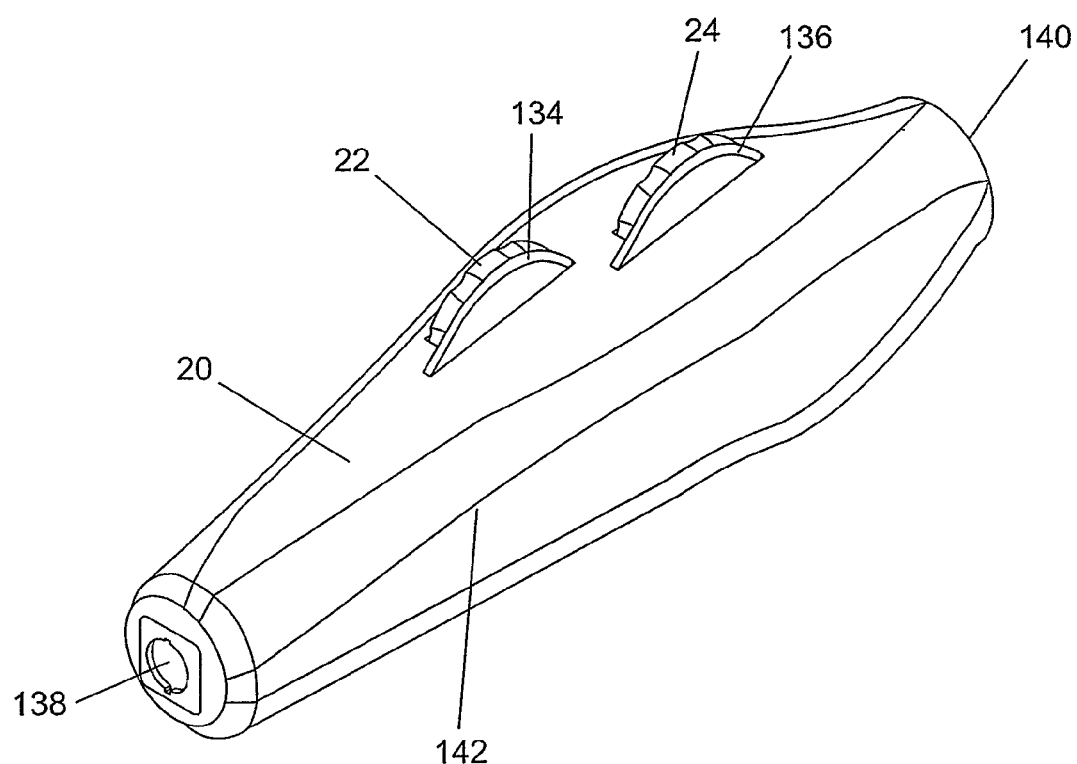
FIG. 18 is a detailed illustration of a catheter handle.

FIGS. 3-8 and 18-21 illustrate detailed construction of the catheter assembly 10 of the first exemplary embodiment. FIG. 18 illustrates the handle 18 with the catheter shaft 12 and the strain relief 26 removed to show a proximal orifice 138. Cable wires 28 from the connector 30 extend through a proximal orifice 138. The catheter steering mechanisms and signal wire bundle extend through distal orifice 140.

It can be seen that the contour of the handle facilitates one-hand use. The lower portion of the thumb and the two smallest fingers comfortably grip the handle 18 at a grip area 142. The shape of the handle 18 and positioning of the actuators 22 and 24 permits easy access for the thumb on the top of the handle and either the index or middle finger on the bottom of the handle to manipulate either the first steering actuator 22 or the second steering actuator 24 while maintaining hold on the grip area 142 of the handle 18.

Figure 19:
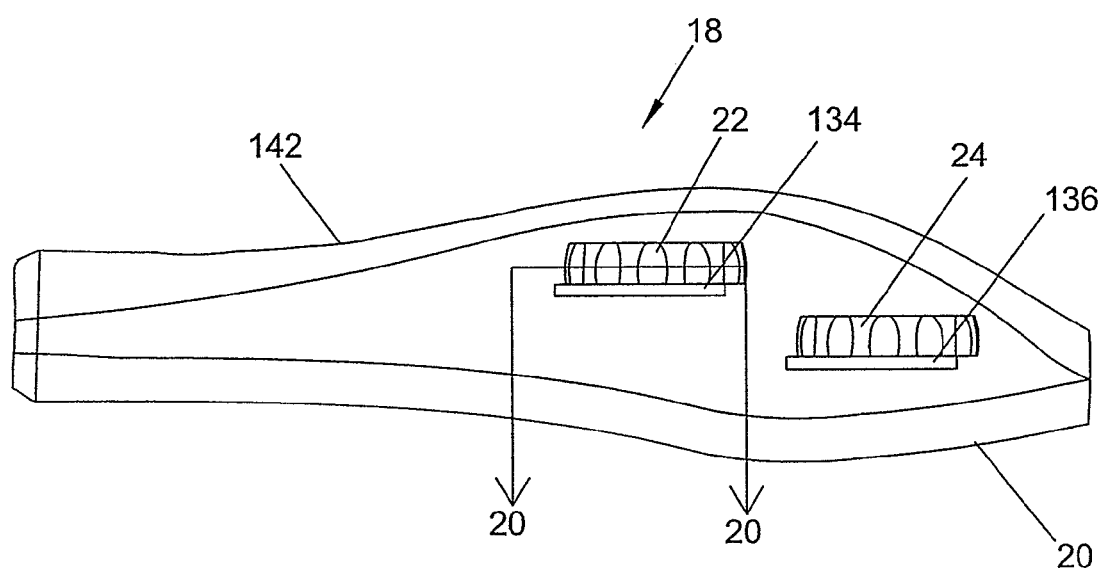
FIG. 19 is a top view of the same catheter handle.

FIG. 19 illustratively depicts a top view of the handle in FIG. 18 to more clearly show the offset (staggered) alignment of the two actuators 22 and 24 with regard to a shared surface of the handle 18's housing 20. With continued reference to FIG. 18, a first lock lever 134 and a second lock lever 136 protrude slightly above the outer edges/diameters of the first steering actuator 22 and second steering actuator 24. While in the resting locked position shown, the locking mechanisms controlled by the levers 134 and 136 do not allow the actuators 22 and 24 to be moved, thus maintaining the catheter 10 in its desired rotational and flex state. While a user's thumb manipulates one of the actuators 22 and 24, the associated one of the lock levers 134 and 136 is held down slightly by the thumb, releasing the corresponding locking mechanism and allowing the actuator to be moved (e.g., the knob rotates).

It can be seen from FIG. 18 that the contours of the actuators 22 and 24 and lock levers 134 and 136 are configured so that it takes a small amount of force to hold the lock levers 134 and 136 down, and the thumb slides easily over the lock lever 134 and 136's surface while moving the corresponding actuator 22 or 24. After the actuator 22 or 24 is moved to the desired position and the thumb is taken off the lock lever 134 or 136, the corresponding lock automatically engages the actuator 22 or 24, holding the actuator 22 or 24 in the desired position until the next time it is to be moved.

Figure 20:
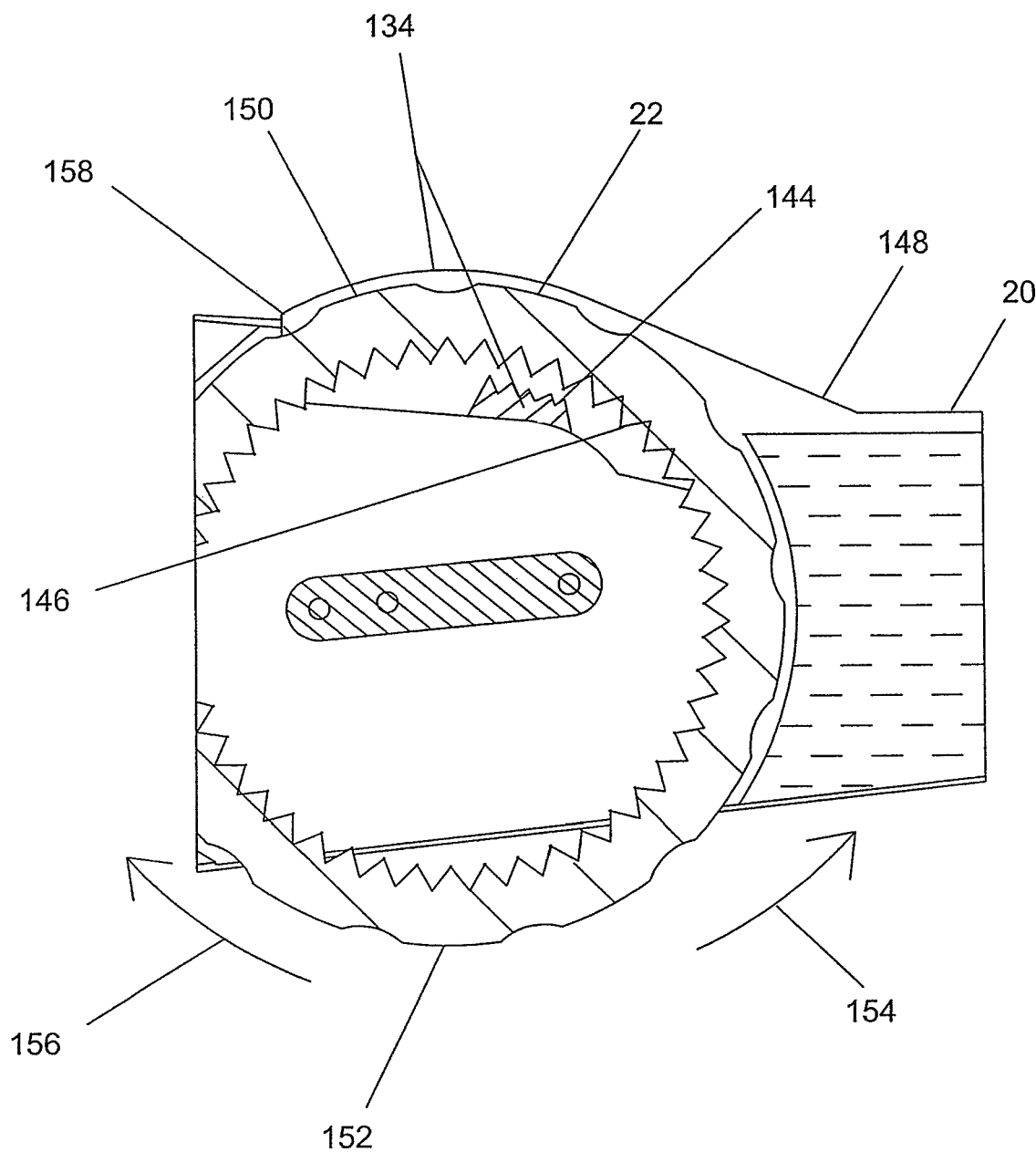
FIG. 20 is a cross-sectional view of the locking/unlocking mechanism in one of the knobs of the catheter handle.

FIG. 20 illustrates an exemplary configuration for the locking mechanism on the actuator 22 (taken along section line 20 in FIG. 19), though other configurations such as a clutch (see, e.g., FIGS. 24 and 24A described herein below) are contemplated in alternative embodiments. The first lock lever 134 is attached at one end to the handle 18 and has a free floating lock lever end 158 at the other end. The first lock lever 134 has a flexible portion 148, made, for example from a flexible polymer that is within its elastic limit over the flexible locked/unlocked displacement range used in the locking mechanism. Exemplary polymers include polycarbonate, acetal (such as Delrin® acetal resin), or any hard—yet flexible—plastic.

FIG. 20 illustrates the lock 134 in an unlocked position in the handle 18. Note an upper thumb surface 150 and a lower finger surface 152. The first lock lever 134 contains lock teeth 144, which, when in the unlocked position, are not engaged with steering knob teeth 146. In this position while the first lock lever 134 is held down and the flexible portion 148 is flexed, the first actuator 22 is turned to the desired orientation or angular position. When the first lock lever 134 is released, lock teeth 144 engage with steering knob teeth 146 and the first actuator 22 is locked in its angular position.

Though the embodiment shown in FIG. 20 utilizes the engagement of teeth as an actuator locking mechanism, in an alternative embodiment the teeth locking mechanism is replaced by a friction surface on the lock that when engaged to a surface of the actuator (e.g. the wheel), the friction surface creates a holding force. The friction on the steering actuator's surface can be created by using a rough surface, or an elastomeric material like silicone, thermoplastic elastomers or rubbers, or a tacky material. In addition, though a radial engagement of the locking mechanism is shown, alternatively, the mechanisms as described can be incorporated in the axial direction.

Figure 24:
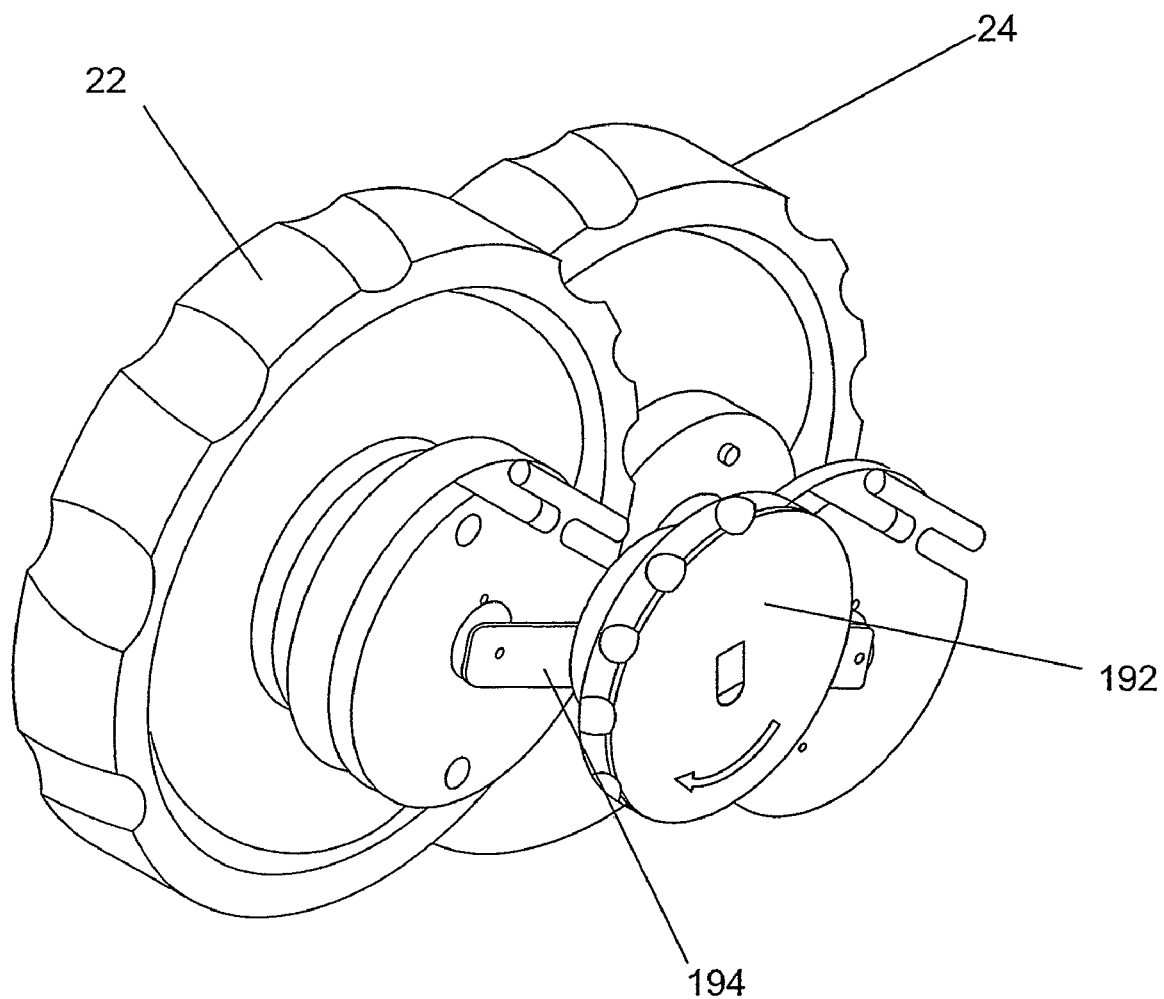
FIGS. 24 and 24A is a detailed view of a clutch in relation to the knobs.
Figure 24A:
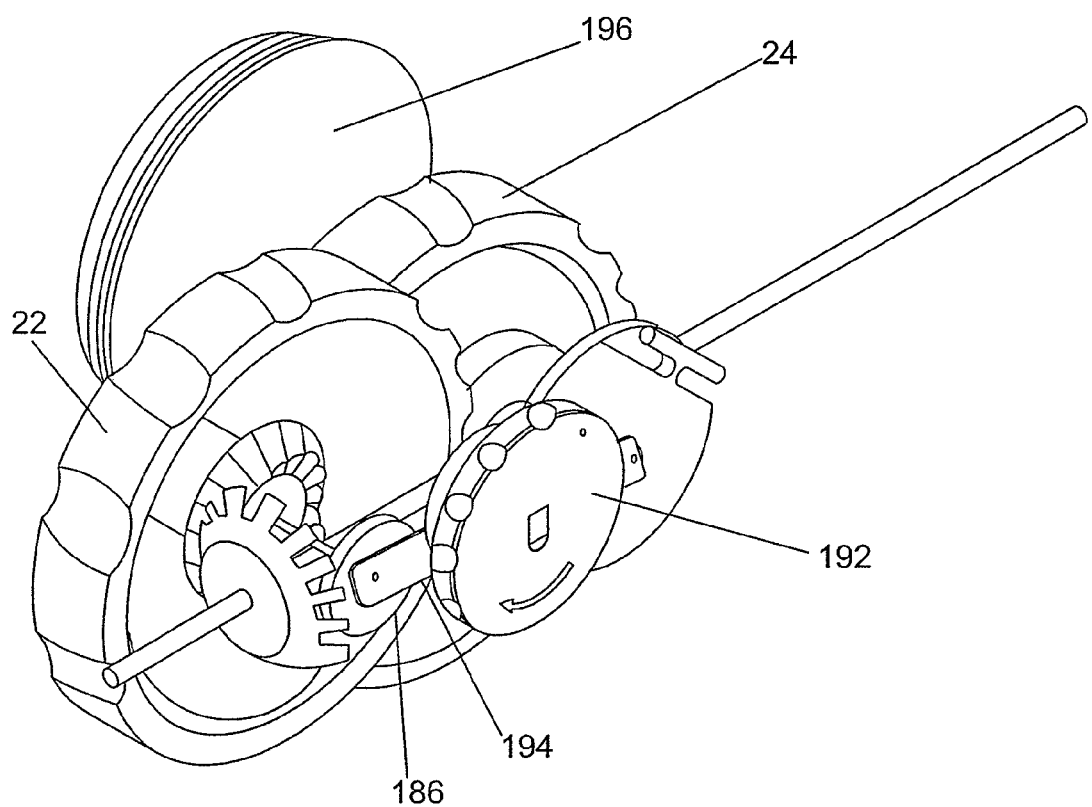

Alternatively, referring to FIGS. 24 and 24A, the locking mechanism is provided by a clutch that includes a tensioning knob 192, a friction cone 196 and the actuators 22 and 24. The tensioning knob 192 generates a lateral displacement pushing the actuator 24 into further contact with the friction cone 196 resulting in a greater level of resistance to rotational motion. A similar cone (not shown) exerts resistance on the actuator 22. The controllable additional resistance provides greater controllability to hold the actuators 22 and 24 against the restoring force presented by the steering lines that are in tension to maintain a desired position of the transducer probe mounted on the rotatable tip 34.

Figure 3:
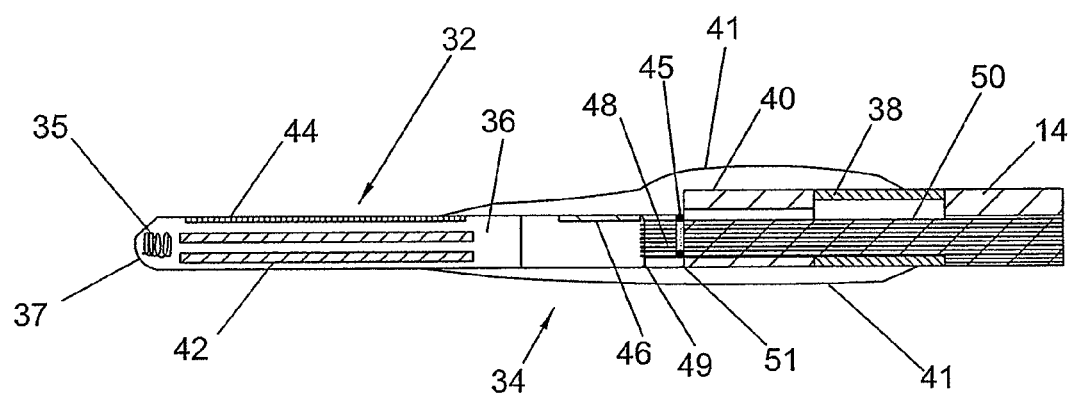
FIG. 3 is a section taken along line 3 in FIG. 2.
Figure 4:
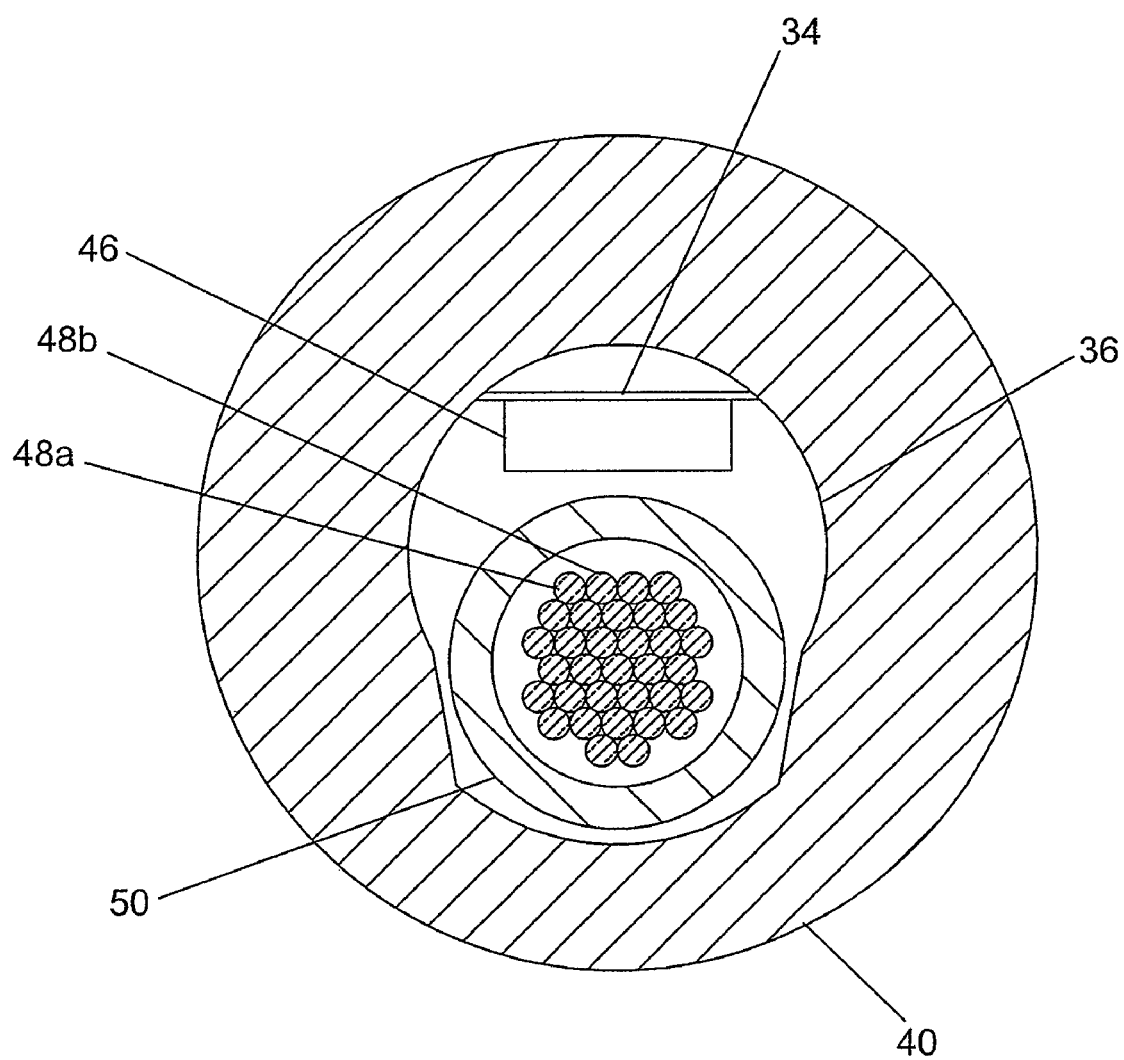
FIG. 4 is a cross-section taken along line 4 in FIG. 2.
Figure 5:
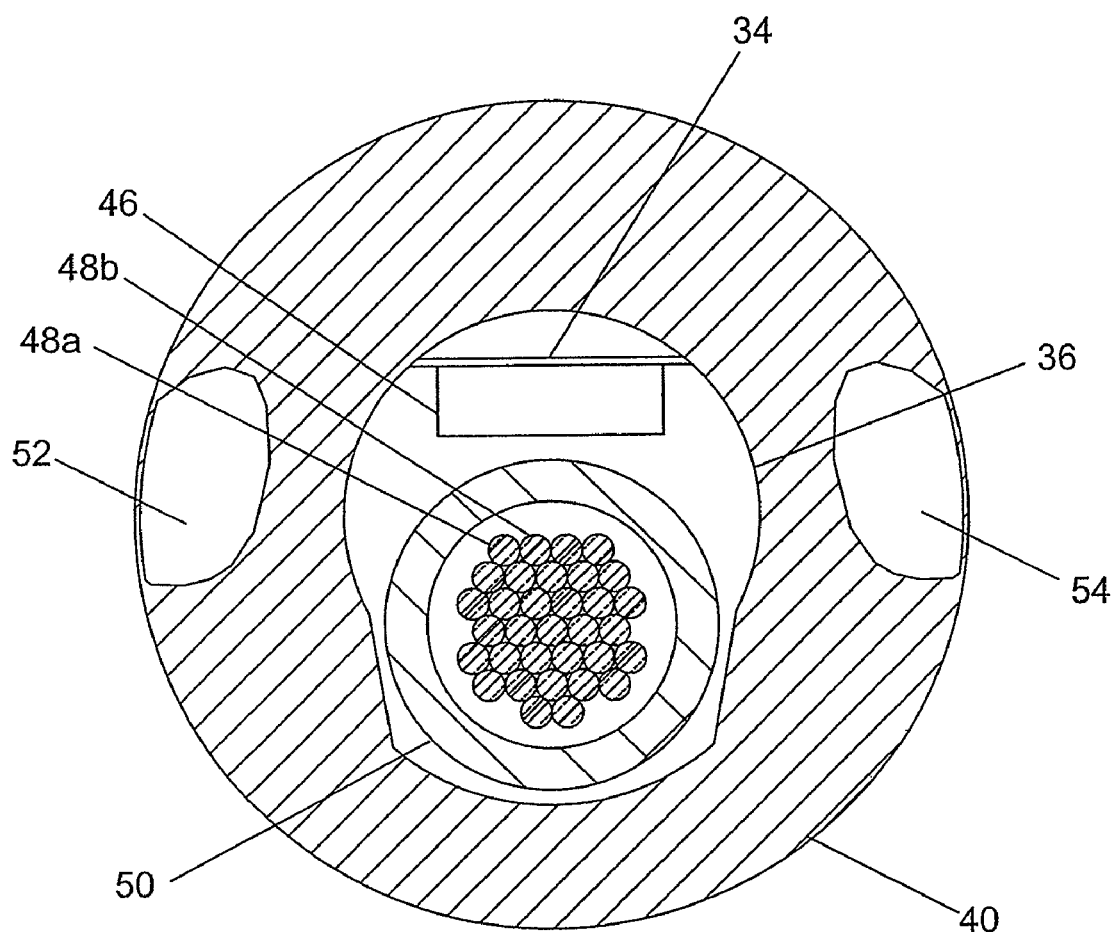
FIG. 5 is a cross-section taken along line 5 in FIG. 2.

FIG. 3 illustrates an exemplary embodiment of the rotatable tip 34. The rotatable tip 34 has a length that typically is 10 mm, and ranges from 5 mm to 20 mm. The exemplary transducer array 32 includes 64 transducer elements 44 mounted on a backing material 36. Inside the rotatable tip 34 is a stiffening member 42 proximate to the transducer elements 44. The stiffening member 42 can be a tube or rod, or can be of noncircular cross-section. Stiffening member 42 is made, for example, from a stiff material, such as a metal. The stiffening member 42 is made, for example, of a radiopaque metal, such as platinum, though stainless steel of sufficient wall thickness is sufficiently radiopaque. Alternatively the transducer array 32 is large and stiff enough on its own, so that the stiffening member is not needed.

The chip 46 is shown and provides for multiplexing, signal amplification or a combination of both as described earlier. A rotation point 51 represents the portion on the rotatable tip 34 that interfaces with the distal segment termination 40 on the distal segment 14 of the catheter shaft 12. The distal segment termination 40 is made, for example of engineered nylon (such as Pebax® polyether block amide). Attached to the rotatable tip in this embodiment is a torque member 50, made of a torquable tube, for example a braided or coil reinforced tube. It can also be made from a co-extruded tube. This tube can also act as electromagnetic interference (EMI) shielding. A cable bundle 48 is shown inside the torque member 50. The cable bundle 48 can be coaxial or simple wire, etc. Each of the cables of the cable bundle 48 is terminated to electrical connections 49 interfacing with the integrated circuit chip 46.

As FIGS. 3-8 illustrate, when the first steering actuator 22 is moved, end piece 40, steering bulkhead 38, and catheter shaft 12 remain rotationally static, but torque member 50, cable bundle 48, and rotatable tip 34 all rotate together to the desired angular position.

To prevent blood from entering the central lumen 47 of the catheter shaft 12, a seal 45 such as an O-ring seal is placed at the rotation point 51 that allows the rotating components to rotate but serves as a barrier for blood to enter. In addition, a flexible sheath 41 connects and covers the tip 34 and distal segment 14 of the catheter 12 and provides for the tip 34 to rotate bidirectionally relative to the distal segment 14 by at least 360 degrees in each direction. In addition the sheath 41 provides a seal for the tip and distal segment of the catheter 12 from bodily fluids. The ends of the sheath 41 are thermally joined/fitted to the tip 34 and distal segment 14 of the catheter 12 to form a seal.

Figure 21:
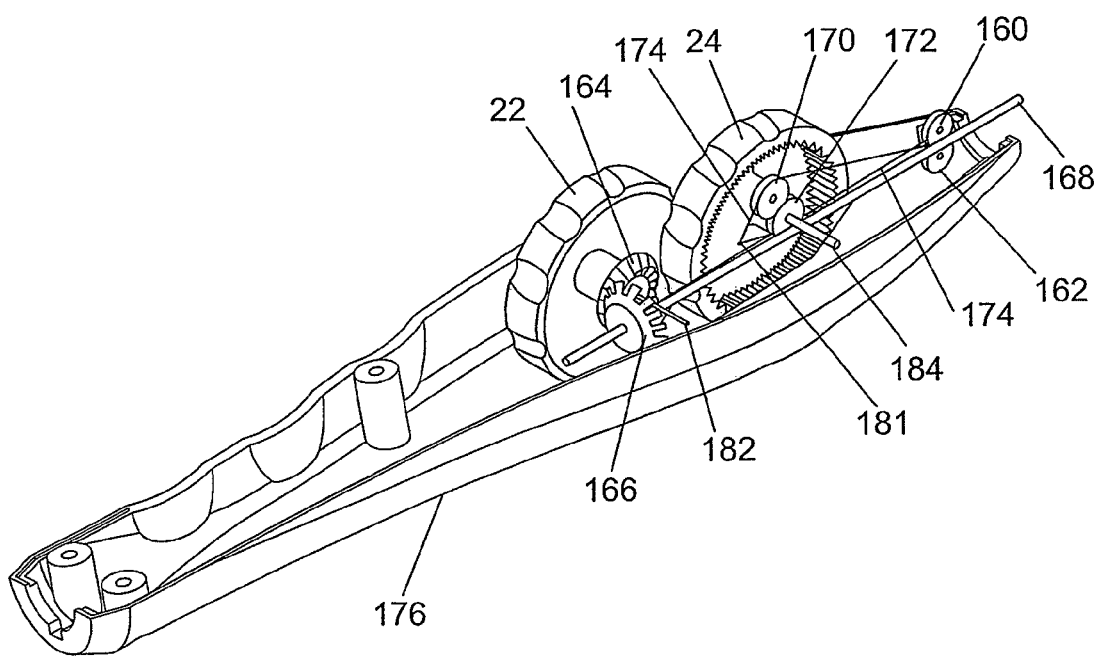
FIG. 21 is a detailed internal view of a first embodiment of the catheter handle for use with a catheter having a combination of rotational steering and flexed steering.

FIG. 21 is a detailed internal view of the first embodiment of the catheter handle 18 for use with a catheter having a combination of rotational steering and flexed steering. FIG. 21 illustrates a gearing interface that enables the first actuator 22 to turn torque member 50, which turns the cable bundle 48 and the rotatable tip 34. The lock levers and top housing half of handle 18 are not shown in order to more clearly illustrate the gearing interface.

The first actuator 22 is rotated around a first shaft 182 causing actuator gear 164 to turn shaft gear 166. Shaft gear 166 is attached to a stiff torque shaft 168, which torque shaft is in turn attached to the torque member 50 in the catheter shaft 12. Alternatively, the torque member 50 is directly attached to shaft gear 166. As illustrated in FIGS. 20-21, when the first actuator 22 is rotated in a first rotational direction 154, the stiff torque shaft 168 is rotated clockwise. When the first actuator 22 is rotated in a second rotational direction 156, the stiff torque shaft 168 is rotated counter-clockwise. Though a beveled gear pair is illustrated, alternatively other gearing mechanisms can be used, such as a worm and wheel combination.

Figure 8:
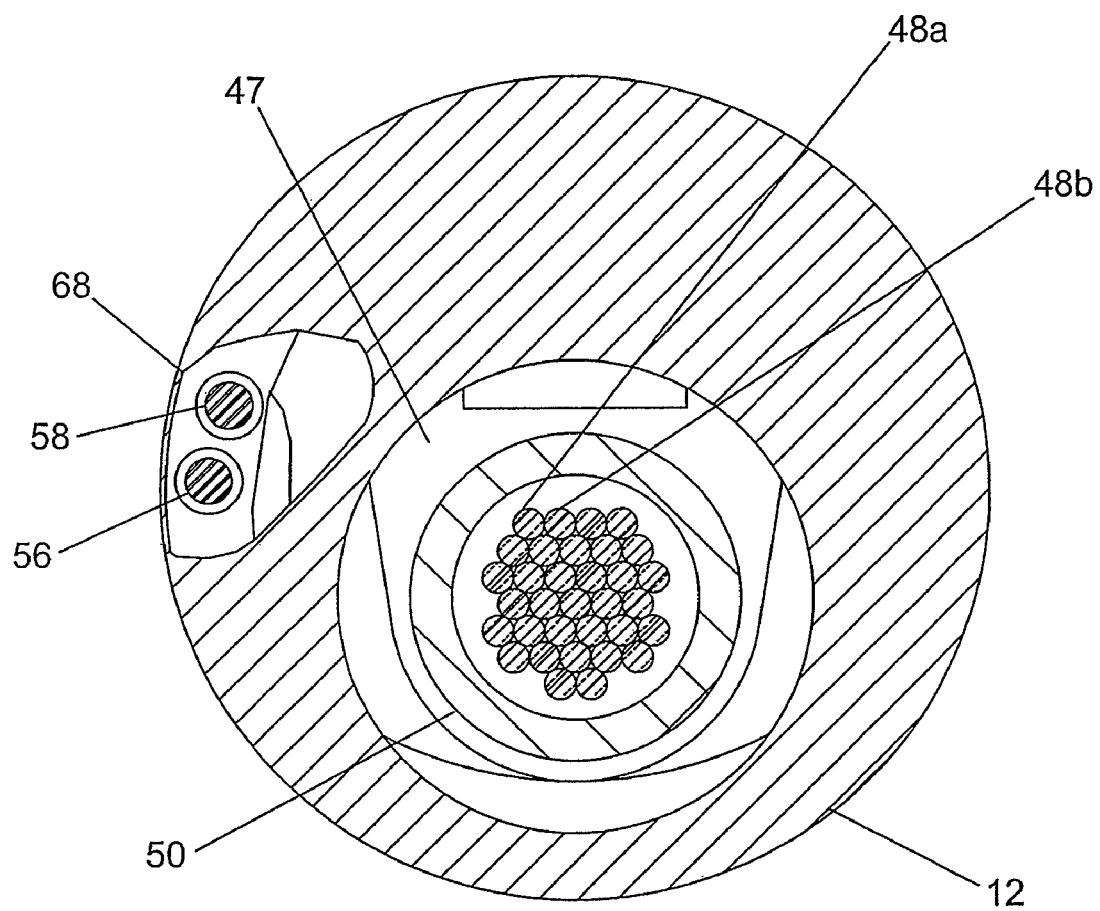
FIG. 8 is a cross-section taken along line 8 in FIG. 2.

FIG. 8 illustrates a cross section of the catheter shaft 12 over the majority of its length. The catheter shaft 12 includes central lumen 47 containing the wire bundle 48 including individual wires (e.g., 48a and 48b) and a shared lumen 68 through which the first steering wire 56 and the second steering wire 58 pass. Each steering wire can alternatively be within its own sheath (not shown), and both assemblies of wire and sheath are contained within the shared lumen 68.

Figure 7:
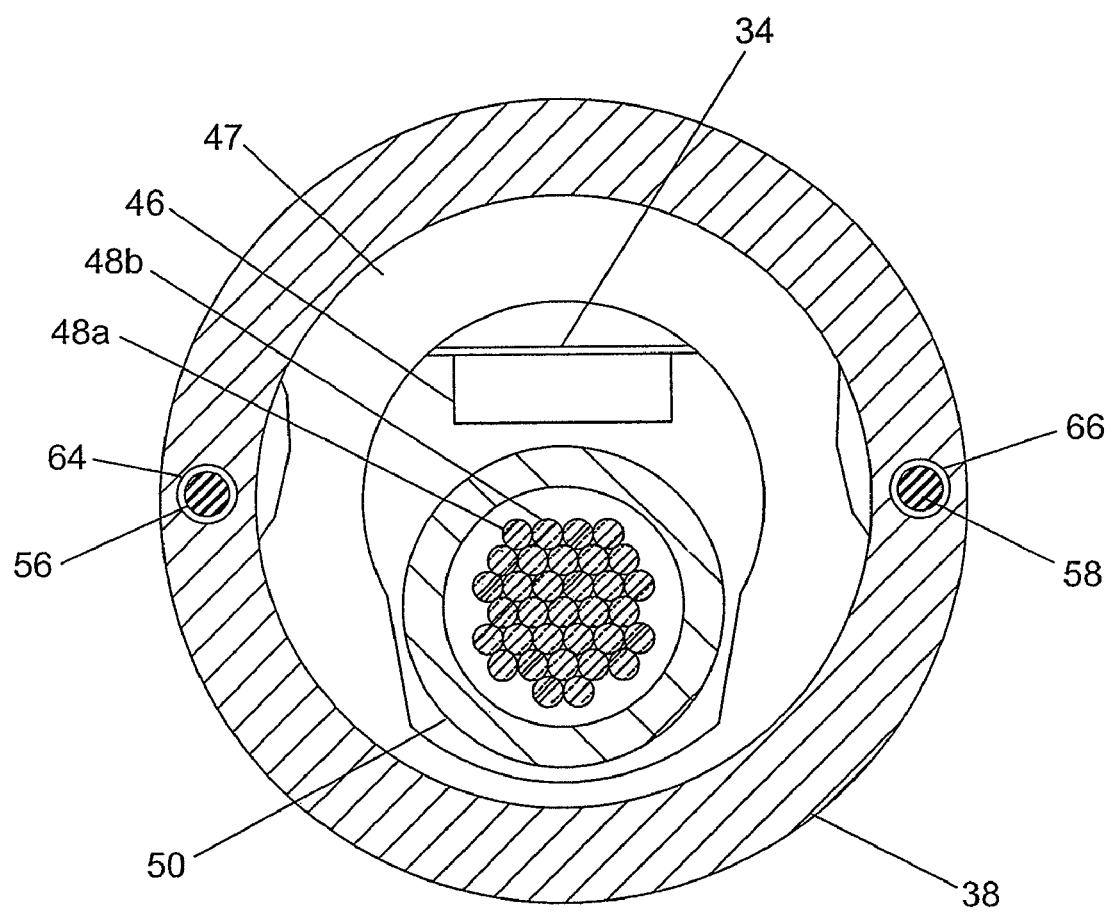
FIG. 7 is a cross-section taken along line 7 in FIG. 2.

Further distal, as illustrated in FIG. 7, the catheter shaft 12's configuration at steering bulkhead 38 includes a cross section having central lumen 47, as well as first steering lumen 64 and second steering lumen 66, through which the first steering wire 56 and the second steering wire 58 pass individually. In between the proximal and distal ends of the catheter 12 having exemplary cross sections illustrated in FIGS. 8 and 7, the assemblies of wire and sheath transition from the shared lumen 68 to the separate steering lumens 64 and 66.

Figure 6:
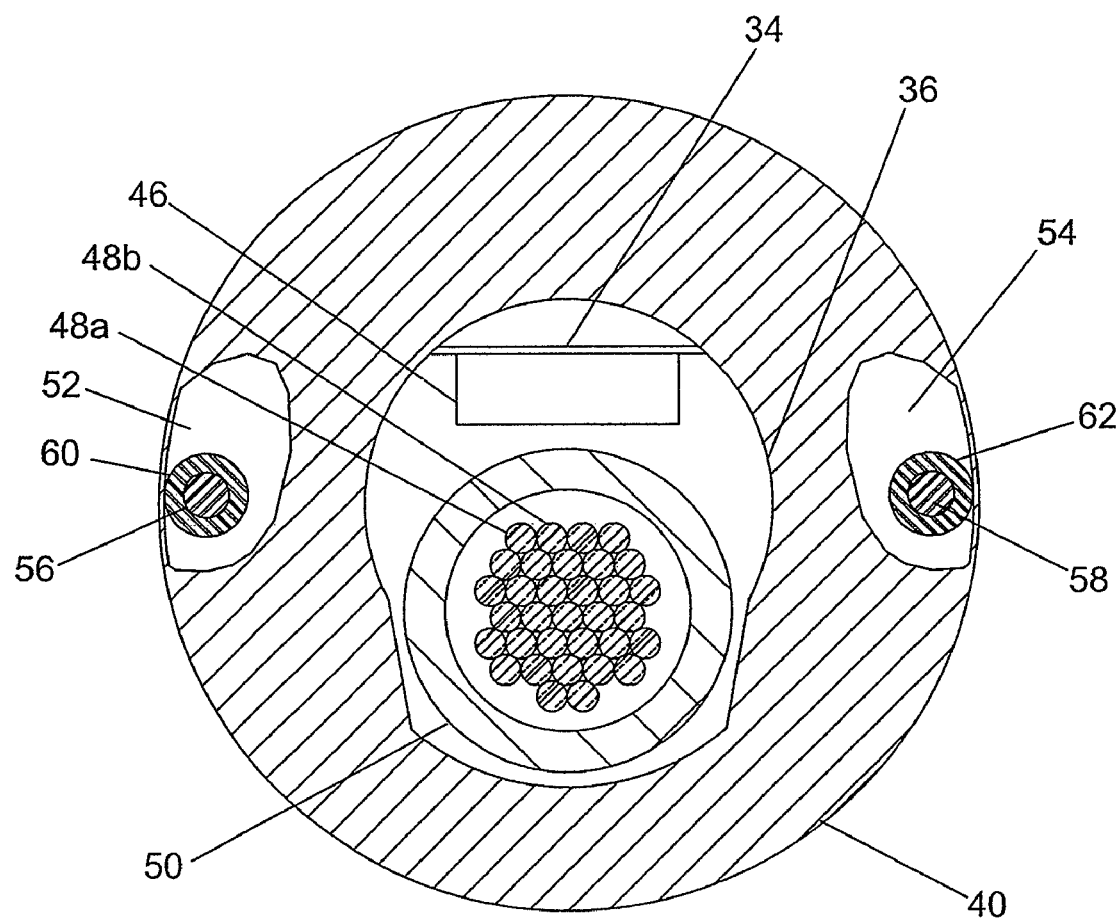
FIG. 6 is a cross-section taken along line 6 in FIG. 2.

FIG. 6 shows the portion of the distal segment termination 40, at which the distal ends of both of the steering wires 56 and 58 are located. Steering wires are alternatively called steering lines. Attached or secured to the ends of the steering wires are a first end cap 60 and a second end cap 62. As an alternative method to connect and attach or secure the steering wire to the distal segment of the catheter, a single steering wire turns around at the end piece 40, secures to the distal ends of the steering lumens by tension and adhesive for example, and runs continuously and bidirectionally inside the catheter shaft 12 from a steering control actuator on the handle 18 without using end caps 60 and 62 to accomplish flexed steering. This configuration can be repeated to enable flexing in two or more directions. The end caps 60 and 62 or alternatively the continuous loop steering wire are attached to the distal segment termination 40 using adhesive, solder, welding, brazing, swaging, crimping, or other attachment methods. The steering wires 56 and 58 are made, for example, of stainless steel or nitinol, but can also be made of aramid fiber (such as Kevlar® aramid fiber) or other high tensile types of line, and thus, the steering wires 56 and 58 are more generally called steering lines to include a wide variety of metal and non-metal materials. A first clearance lumen 52 and a second clearance lumen 54 allow the end caps 60 and 62 to fit within them, but alternatively the clearance lumens 52 and 54 can be formed permanently around the end caps. The diameter of each end cap 60 and 62 is larger than the diameter of each steering lumen 64 and 66.

By pulling the first steering wire 56 in a proximal direction, the end cap 60 impinges on distal segment of the steering lumen 64 of the steering bulkhead 38, causing this side of the catheter tubing to be stressed, thus causing the catheter shaft 12 to flex in a direction favoring this stress. Since steering wires 56 and 58 are integrally connected and wrap around a steering knob, when the first steering wire 56 is pulled, the second steering wire 58 is extended on the other side of the catheter shaft 12, resulting in a complimentary relaxation in the compliment wire and a smooth catheter profile for flexed steering. When second steering wire 58 is pulled instead of first steering wire 56, the opposite occurs and the catheter shaft flexes in the opposite direction.

In the catheter shaft as illustrated in FIGS. 3, 6-8 the cable bundle 48 that includes wires 48*a* and 48*b* has a substantially uniform diameter and radial symmetry in the wire bundle 48, such that the bending stiffness is substantially uniform in any plane or surface in flexed steering of the catheter shaft 12 in the present catheter assembly 10. The cable bundle 48 is contained in free form tubing that is soft and compliant to enable the cable bundle to fit easily and symmetrically inside a lumen or cavity. For the operator of the present system this uniform bending stiffness enables easy and accurate control for improved manipulation or maneuverability to navigate and orient the transducers to an optimal position and orientation to image a target area in an intracardiac chamber such as an atrial chamber.

In an alternative to the configuration of FIG. 8, the shared lumen 68 is located more centrally in the catheter shaft 12. Alternatively, the steering lumens 64 and 66 pass through the central lumen 47 of the catheter 12, and there is no shared lumen. Returning to FIG. 21, an exemplary arrangement is illustrated for flexed steering of the catheter shaft 12's distal segment 14. Second steering actuator 24 is rotated around second shaft 184 causing first steering pulley 170 to rotate eccentrically and second steering pulley 172 to rotate concentrically. The knobs and steering pulleys rotate bidirectionally. First steering line 174 is wrapped around both pulleys 170 and 172 in a switch back or "z" configuration. One end of the steering line 174 terminates at an anchor spring 181 that secures to the handle.

The proximal end of first steering line 174 is secured inside the housing 20, and is attached to an anchor spring 181 to maintain tension. As the second steering actuator 24 is turned, the effective length of the first steering line 174 is changed (i.e., increasing or decreasing) depending on the direction the knob is turned. Distally in the handle 18, an upper distal pulley 160 and a lower distal pulley 162 help guide the steering line 174 as it extends into the catheter shaft 12. A second steering line is a mirror image of the first steering line arrangement already described.

Figure 25:
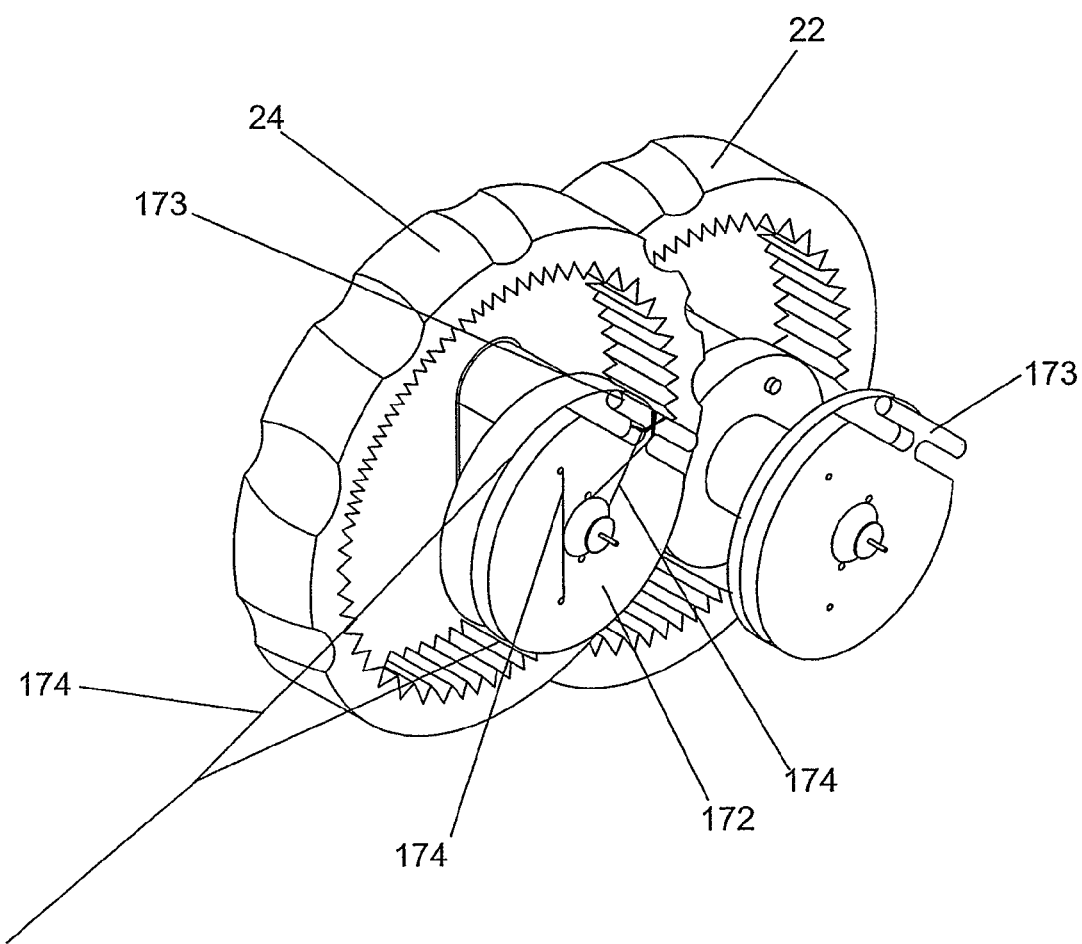
FIG. 25 is a detailed view of a cleat or tie-off mechanism attached to a knob.

As further illustrated in FIG. 25, the steering line 174 alternatively wraps around a steering pulley 172 and a cleat 173 or alternatively called a tie-off mechanism attached to the steering pulley 172 such that steering line 174 departs from the steering pulley 172 and returns to the distal segment 14 of the catheter 12. The cleat 173 provides for proper tension to be set and the reduction or elimination of slack in the steering line 174.

Figure 8A:
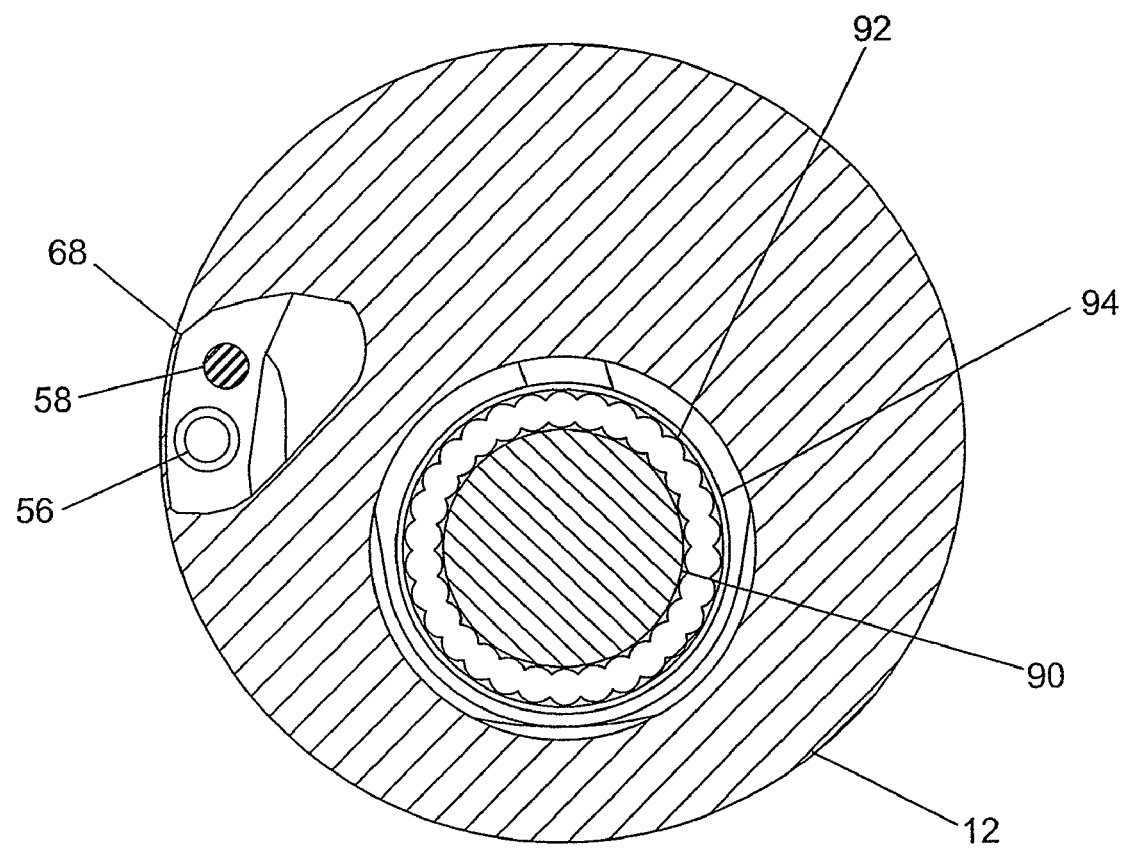
FIG. 8A is an alternative embodiment of the catheter in FIG. 8.

An alternative embodiment of the catheter assembly is illustrated in FIG. 8A. In contrast to FIG. 8, the embodiment of FIG. 8A includes a torque cable 90 which allows the conductors, shown as a flat conductor assembly 92, to be located outside the torque cable 90, not inside a lumen. The torque cable 90 is made from multiple layer multifilar coils. The advantage to this configuration is that a cable of this type can be made to be very straight and thus have a better fine torque response than a torque tube configuration. In this embodiment, the flat conductor assembly 92 can be made from a flex circuit ribbon. The conductor assembly 92 and torque cable 90 have radial symmetry in the catheter shaft such that this configuration has the advantage of substantially uniform bending stiffness in any bending plane in flexed steering as already described. A surrounding tube 94 is made from shrink tubing, and holds the entire assembly together. Another advantage to this embodiment is that the torque cable 90 can extend further into the rotatable tip 34, to secure it, and also allows for easier routing of the conductors at the tip 34 for electrical connection to the cable bundle 48. Electrical connection can be achieved by micro-welding or soldering, or other known methods.

Figure 11:
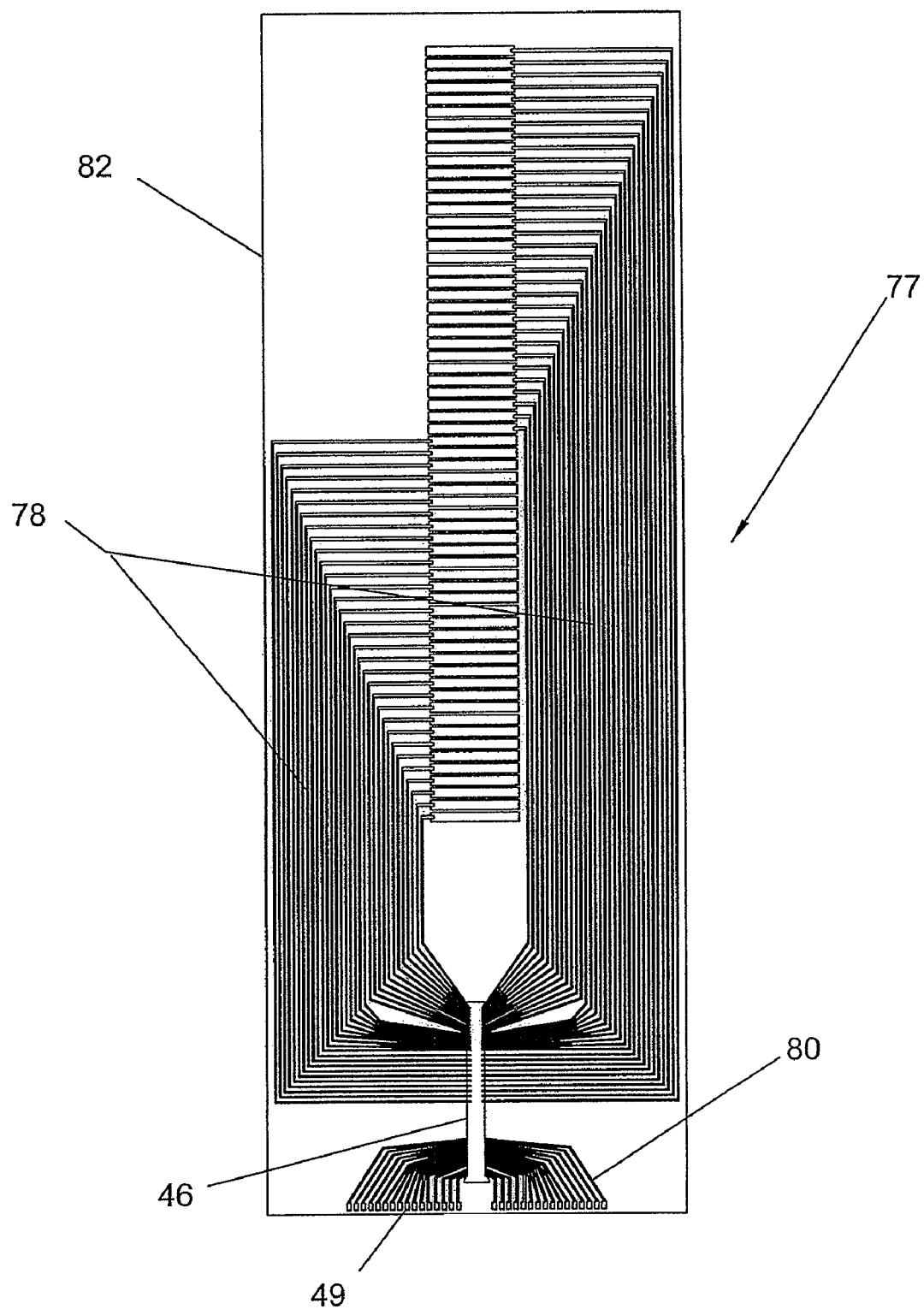
FIG. 11 is an illustration of a flex circuit for use in an ultrasound catheter.

FIGS. 11-14 illustratively depict components of an exemplary tip 34 that includes a transducer array for use in ultrasound catheters of size 6 F and smaller. FIG. 11 illustrates a flex circuit 77 component of the tip 34. In the transducer array 32 each transducer element can be independently programmed to fire. A substrate 82 is made, for example, from a thin and flexible material, such as polyimide. Some examples of polyimide are Kapton® polyimide or Upilex-S® polyimide. The substrate can also serve as an ultrasonic matching layer. Conductive tracings 78 and 80 create multiple conductors on the substrate 82 which is a part of the flex circuit. Each conductive tracing provides a single electrical conduit for each transducer.

Figure 12:
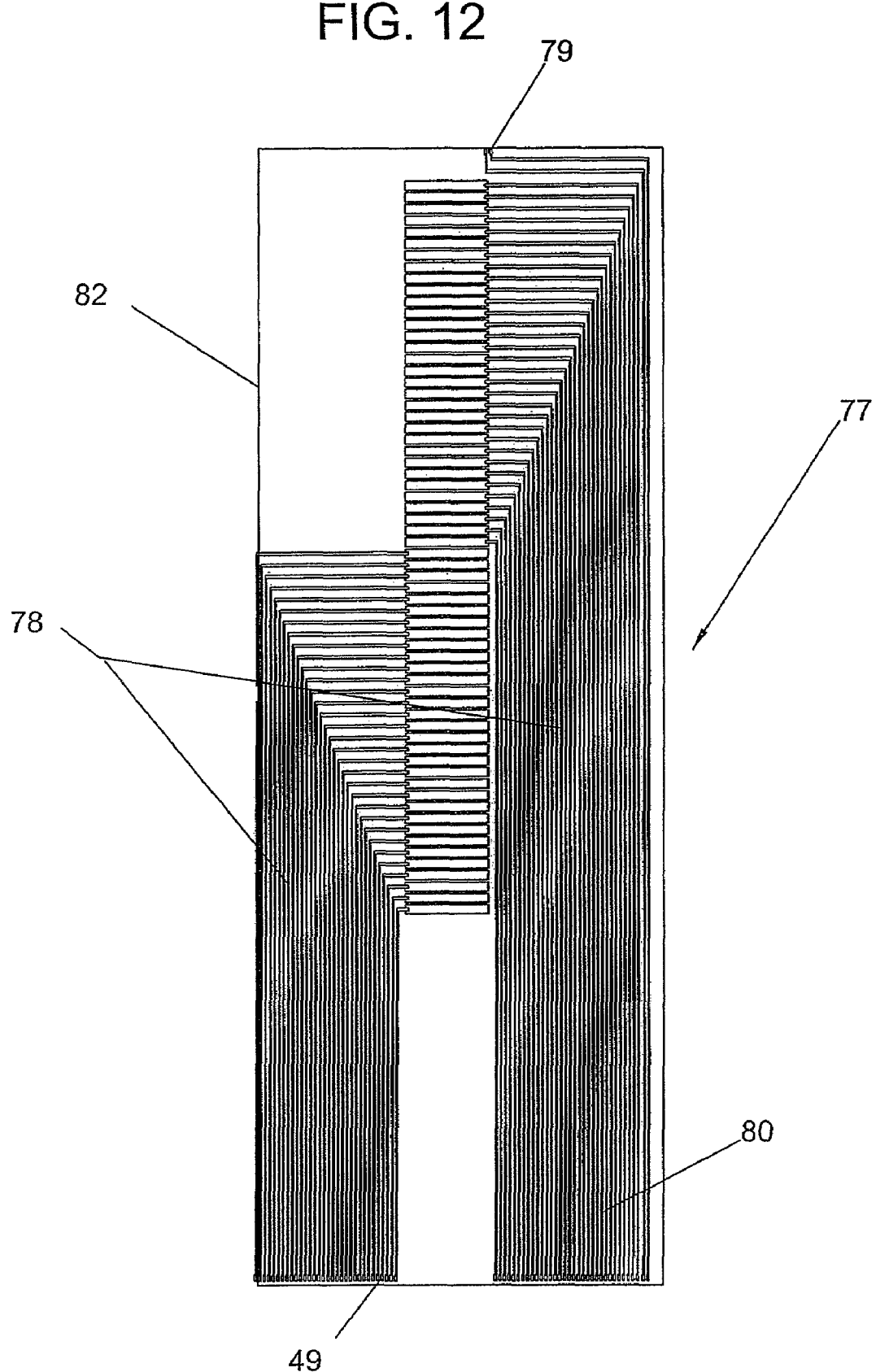
FIG. 12 is an illustration of a transducer/circuit assembly for use in a linear array ultrasound catheter.

In FIG. 12, transducer elements are attached to the flex circuit 77. In one method of fabrication, a piezoelectric material block is attached, and then kerfs are made with, for example, a dicing saw, to create the individual transducer elements. One or more integrated circuit or chip 46 is connected to the conductive tracings 78 and 80. In a specific configuration as illustrated in FIG. 12 the chip 46 is connected between the two groups of conductive tracings 78 and 80. In addition other devices such as a wire loop or RF antenna 35 (see, e.g., FIG. 3) in the tip 34 is connected to conductive tracings 78 and 80 via terminals 79. Terminals 49 allow electrical connection of the aforementioned conductive tracings 78 and 80 to the cable bundle 48. An example of a flex circuit that includes terminals 79 but no integrated circuit is illustrated in FIG. 12.

Figure 13:
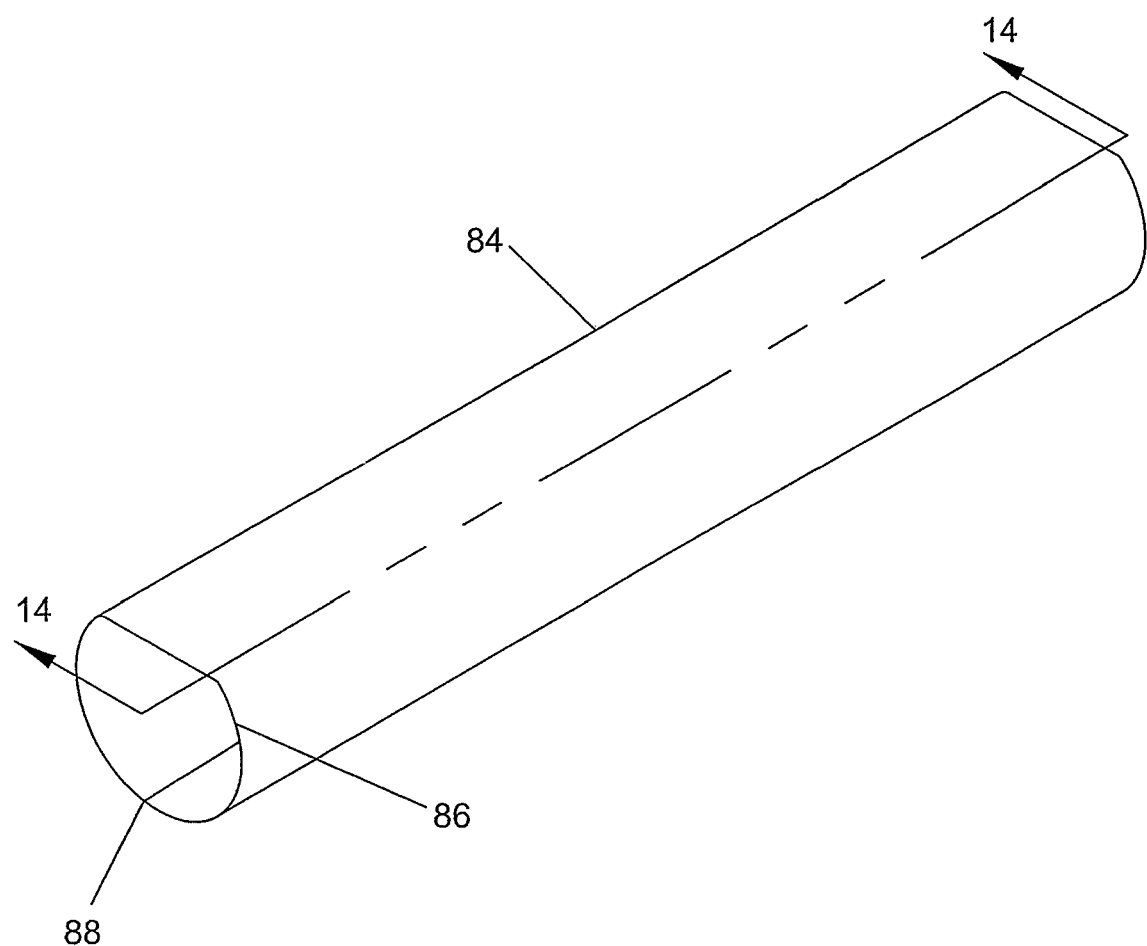
FIG. 13 illustratively depicts the transducer/circuit assembly of FIG. 12 in a rolled or wrapped configuration.
Figure 14:
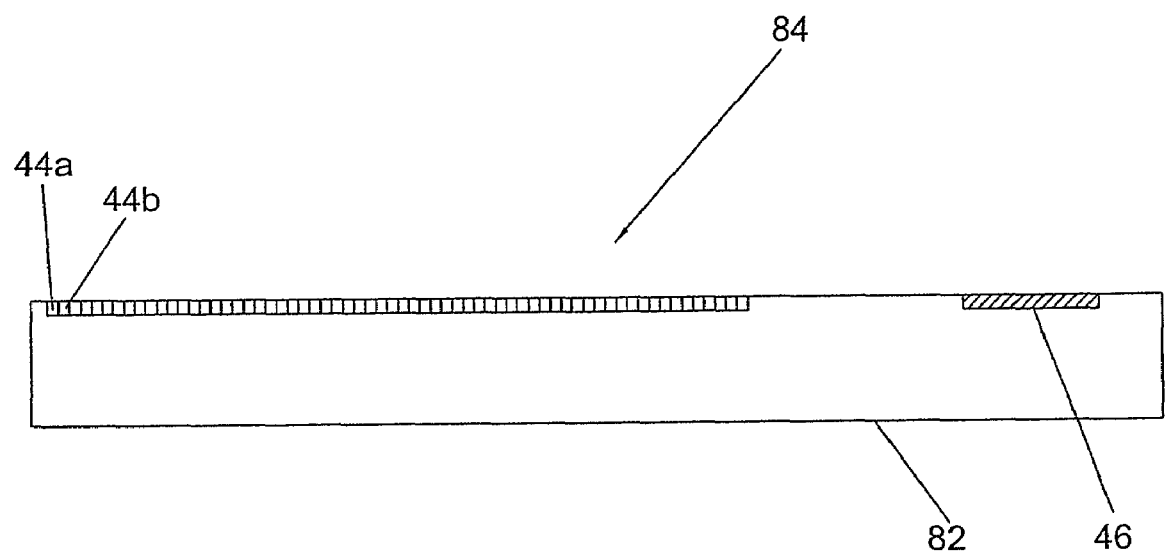
FIG. 14 is a cross-section of the rolled transducer/circuit assembly of FIG. 13 taken along line 14.

In FIGS. 13 and 14 (see also FIG. 3), the assembly of FIG. 12 is rolled into a rolled transducer assembly 84 having a D-shaped cross-section 86 and a seam 88. A distal segment of the flex circuit is rolled over a stiffening member 42 (see, FIG. 3) that is proximate to and extends alongside the array of transducers. The backing material 36 is injected inside the rolled transducer assembly 84. An additional matching layer can be formed over the assembly to provide better acoustic matching between the transducer piezoelectric material and the target tissue as well as the transmission medium. For example, RTV silicone is one such material that can be used. In one embodiment the D-shape cross section allows the linear layout of the transducer elements and uniform wall thickness of the matching layer due to the flat top for even and controlled focusing. The tip 34 has a proximal portion which has a rounded shape and encapsulates the proximal portion of the flex circuit.

Exemplary transducers for ICE have a typical thickness of approximately 0.28 mm in the piezoelectric material to enable an 8 MHz ultrasound signal to be generated and transmitted at a typical velocity of 1500 m/sec through blood. The transducer thickness can be of various thicknesses ranging approximately from 0.56 mm to 0.19 mm to generate sufficient penetration depth in tissue imaging. In general, the thickness of the transducers can be adjusted for the frequency of sound in the transmission medium for the desired penetration depth in any tissue imaging. Image intensity can be adjusted by driving voltage on the transducers.

Figure 15:
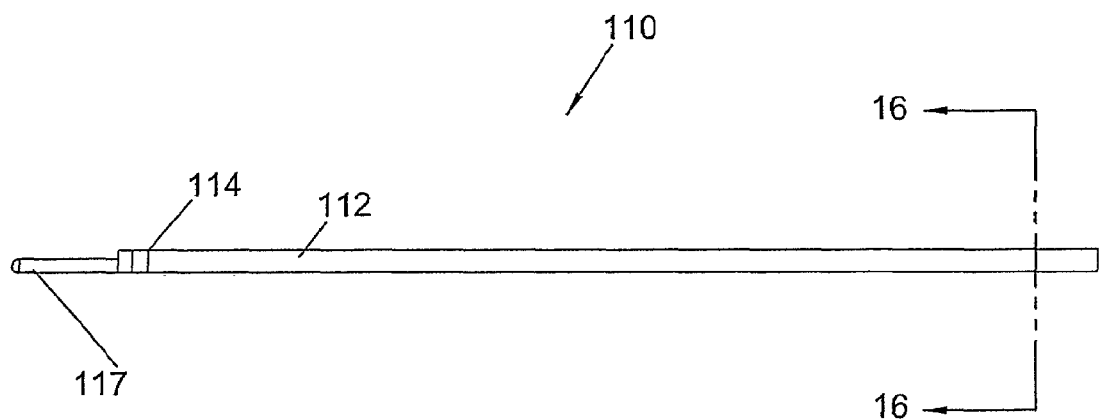
FIG. 15 is an alternative embodiment of an ICE catheter.
Figure 16:
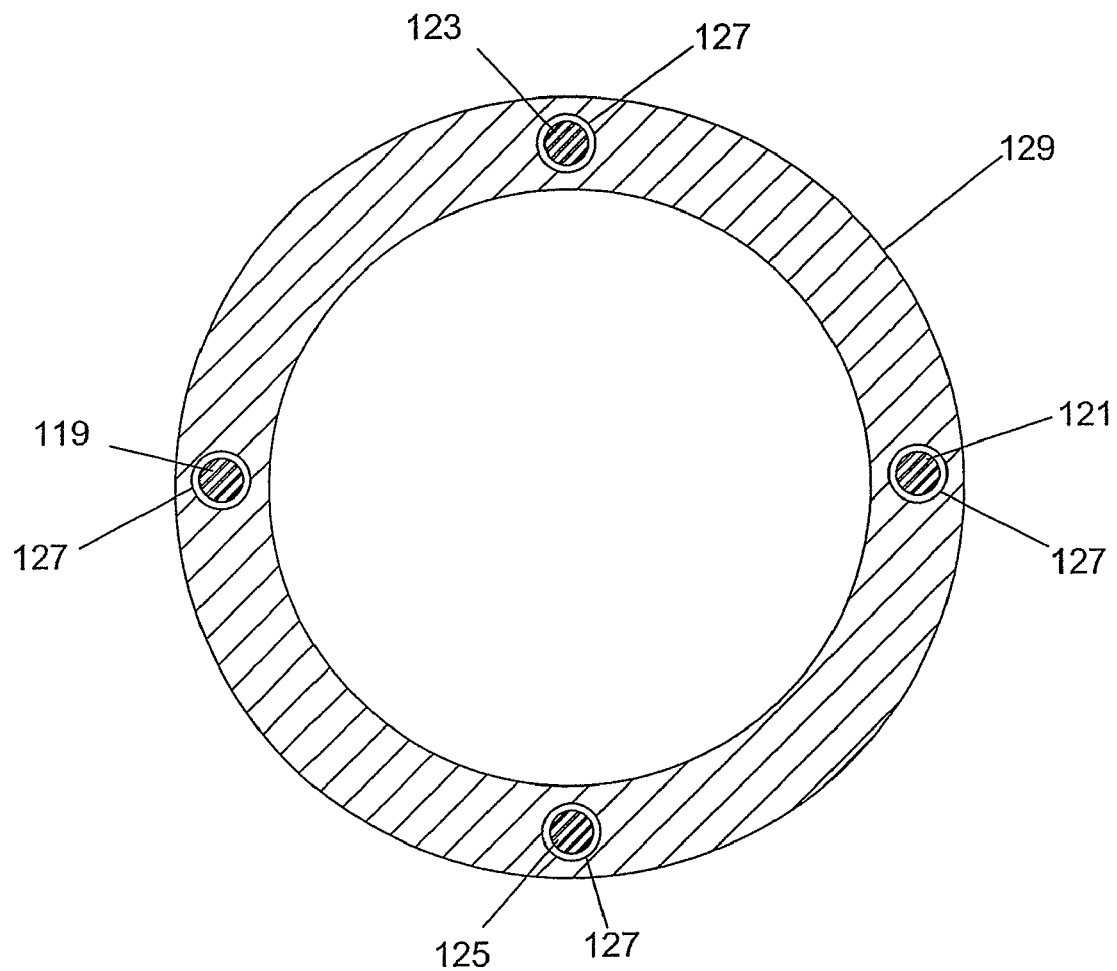
FIG. 16 is a cross-section of the catheter shaft of the catheter in FIG. 15 taken along line 16.

FIGS. 15-16 illustrate an alternative embodiment of the catheter assembly 10. Ultrasound catheter 110 includes a catheter shaft 112 and a distal segment 114 having a non-rotating tip 117. Non-rotating tip 117 has a structure similar to the rotatable tip 34 but differs in its connection with the distal segment of the catheter. Non-rotating tip 117 connects integrally to the distal segment 114 of the catheter shaft 112 and does not rotate relative to the catheter shaft 112. FIG. 16 illustrates two orthogonally arranged planar steering controls. First plane steering lines 119 and 121 and second plane steering lines 123 and 125 pass through four steering lumens in shaft 129.

In an exemplary embodiment, a two-material shaft is provided to overcome stiffness of a high lubricity material. The shaft 129 is extruded so that each lumen has a lumen liner 127 consisting of a material that is different from the material of the shaft 129. The material of the lumen liners is a high lubricity material that allows the steering lines to move axially with minimal frictional resistance. If the entire shaft were to be extruded from the material used in the lumen liners, the high stiffness of the lubricious material used would cause the shaft to be dangerously inflexible. By using an extrusion method that only incorporates this lubricious material into the lumen liners, the rest of the shaft can be made from a sufficiently flexible material to optimize catheter shaft flexibility, ease of use and safety in the patient.

Figure 17:
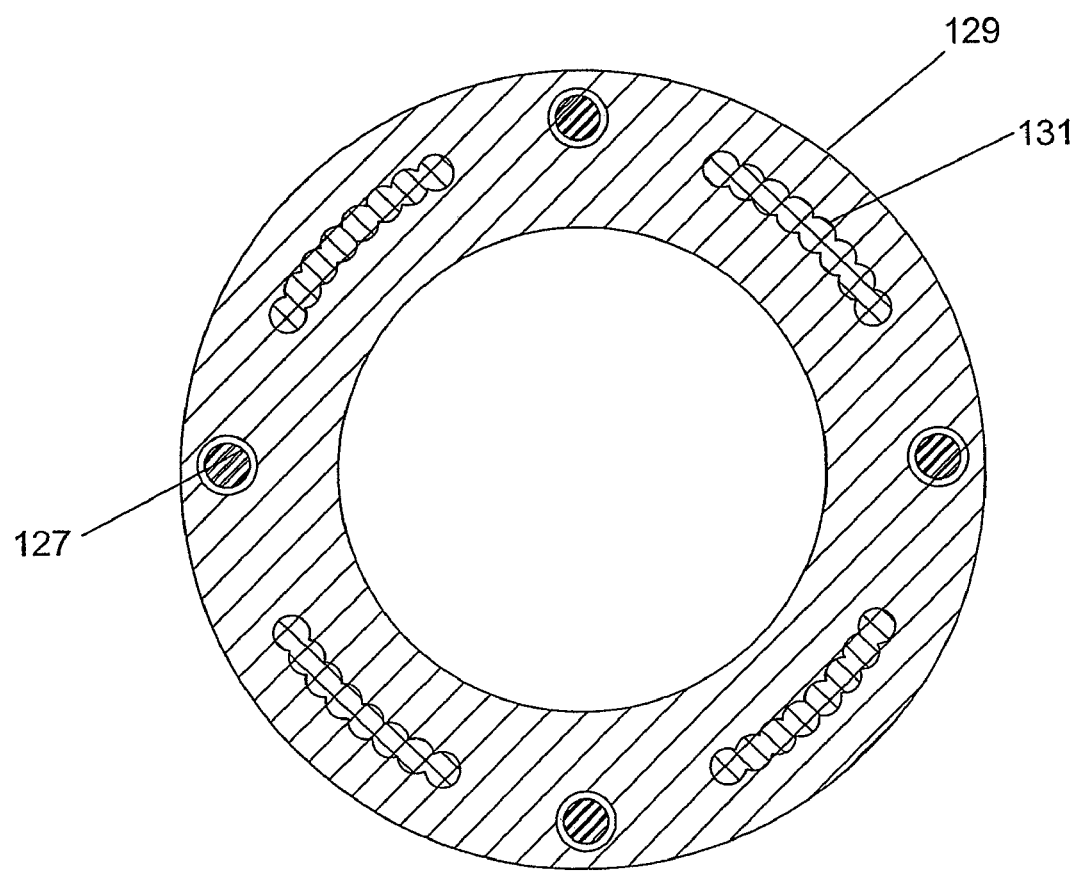
FIG. 17 is a cross-section of an alternative shaft of an ICE catheter.

FIG. 17 shows an alternative tubing extrusion that includes embedded conductors 131 within the tubing wall and extending the length of the tubing. By packaging the conductors in this manner, the wall thickness of the tubing can be increased for strength. At the distal end of the tubing the conductors are well placed for making electrical terminations and further connections to the conductive tracings of the flex circuit. As shown, a flat ribbon of several conductors can be used. In FIG. 17, four groups of eight wire ribbons are illustrated.

Figure 22:
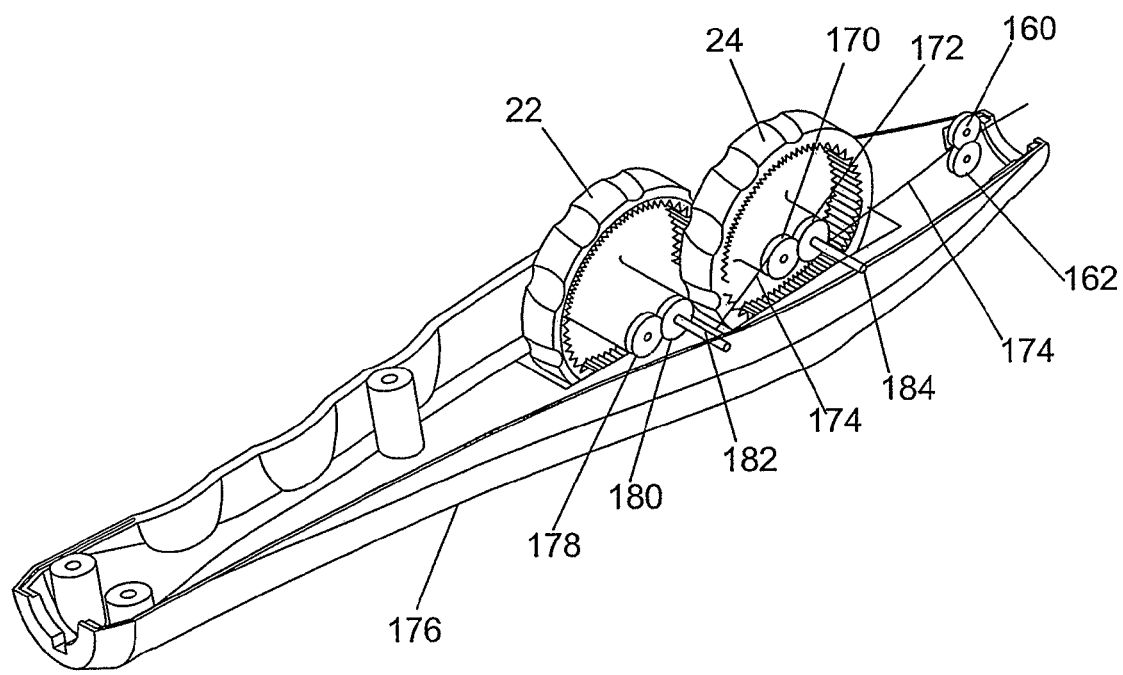
FIG. 22 is a detailed view of a second embodiment of the catheter handle for use with a catheter having two-plane flexed steering.

FIG. 22 illustrates an alternative embodiment of the handle 18 for use with the catheter embodiment of FIGS. 15-17. Second steering actuator 24 works in the same manner as that of FIG. 21. Instead of the gearing mechanism in first steering actuator 22, the embodiment of FIG. 22 contains the same mechanism in both actuators for flexed steering in two different, orthogonal, planes or surfaces. One actuator operates the catheter flexing in a first plane and the other knob operates the catheter flexing in a second plane. First steering actuator 22 operates third steering pulley 178 and fourth steering pulley 180, and its own steering lines (not shown).

Figure 23:
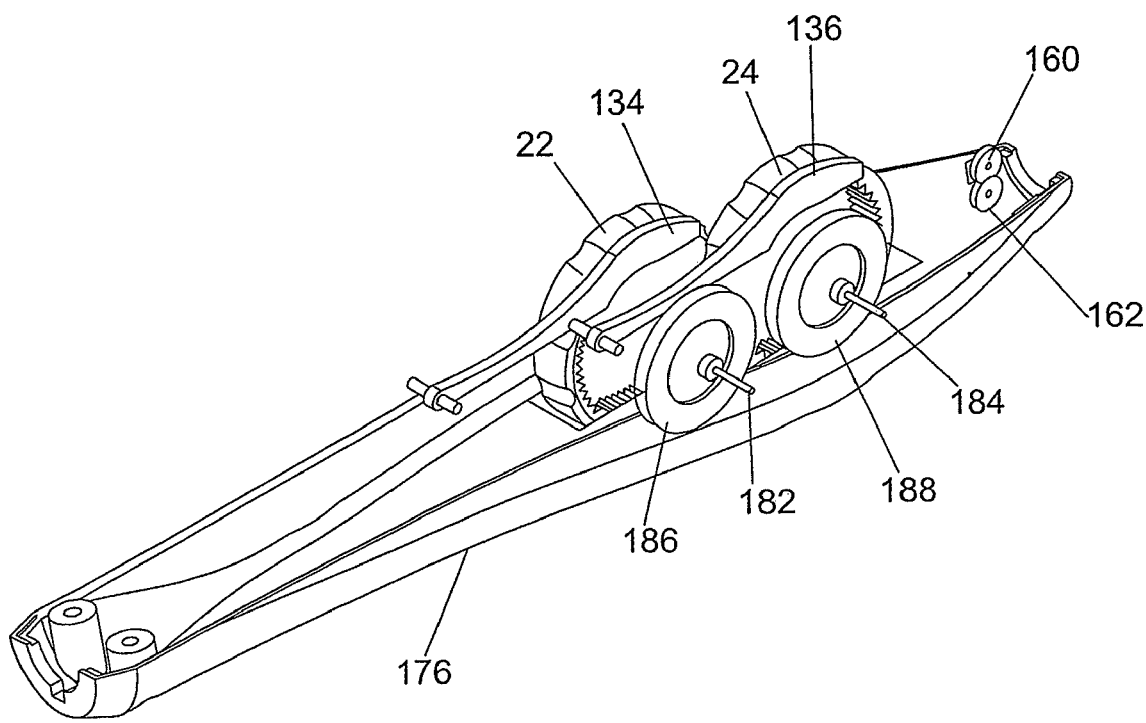
FIG. 23 is a detailed view of a third embodiment of the catheter handle for use with a catheter having two plane flex steering and showing further detail of the locking/unlocking mechanism.

FIG. 23 illustrates a similar embodiment to that of FIG. 22. In place of the two smaller pulleys in each steering knob, each steering knob instead rotates first and second large pulleys 186 and 188. For each plane, a single steering line is used from the distal end in one lumen, then proximally and around the large pulley, and then distally again, terminating at the distal end of the other lumen. The grooves of each pulley are coated with a low lubricity, high friction material, such as silicone elastomer, such that no slippage occurs on the steering line. Alternatively, the steering line is permanently attached to the pulley instead of being frictionally coupled. In this embodiment and all of the other embodiments using steering wire or steering line, tensioners (not shown) consisting of secondary pulleys spring loaded on an arm, can be used to minimize line slack.

In a third embodiment of the present system a three-way steering catheter is made that combines the two orthogonally arranged flexed steering of FIGS. 15-17 with the rotational steering associated with FIGS. 1-14. The three steering modes in this case, for example, are flexed steering left-to-right, flexed steering anterior-to-posterior, and tip rotation. An embodiment of the three plane steering catheter includes the configuration as already described in FIGS. 15-17 and adding a torque member connected to the rotating tip 14 on the distal side and to a third shaft gear assembly on the handle.

Figure 26:
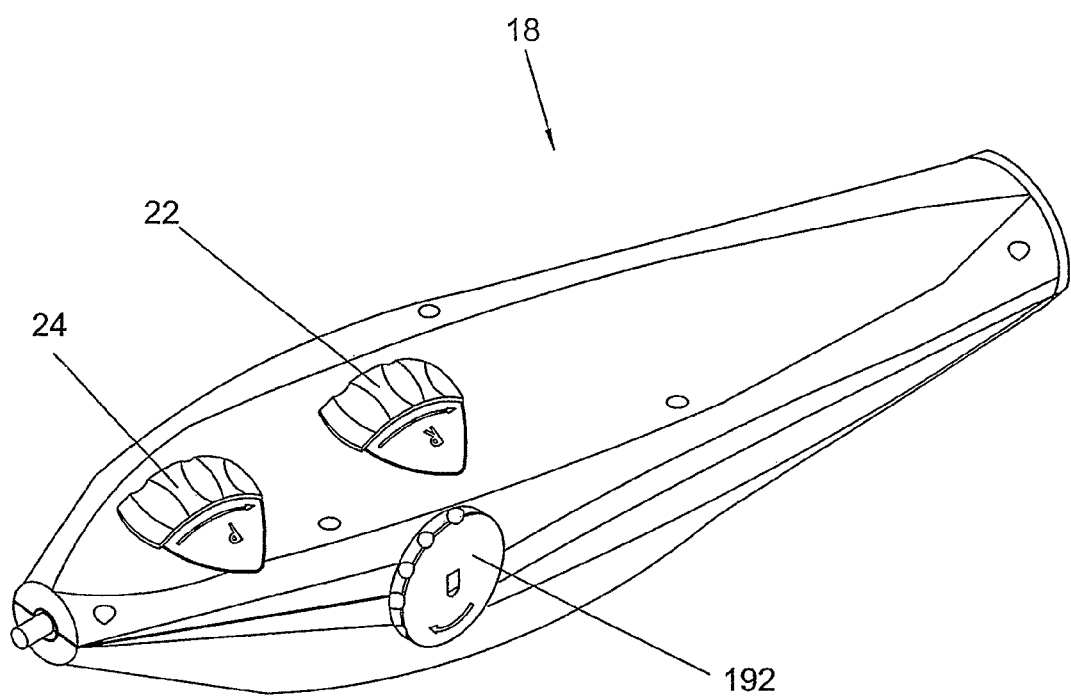
FIG. 26 is a detailed view of a handle with two knobs and a clutch.

FIGS. 24, 24A and 26 illustrate a clutch mechanism facilitated by the interaction of the following components: a tensioning knob 192, a cam 194 (or screw), actuator 24, a thrust washer 186 and a friction cone 196 (not shown in FIG. 24). Actuators 22 and 24 each are fit with friction cones (only friction cone 196 for actuator 24 is shown in the illustrative example in FIG. 24A). The thrust washer 186 acts as an interface between the cam 194 and the actuator 22. Rotating the tensioning knob 192 in a first direction results in the application of lateral displacement to actuators 22 and 24 which, in turn, increases the amount of contact area between the actuators 22 and 24 and friction cones (e.g. cone 196 for actuator 24). The increase in the contact area between the actuators and their corresponding friction cones results in increased resistance to rotational motion of the actuators—which in turn results in increased resistance to the restoring force presented by the steering lines that are in tension. The clutch mechanism acts to create a slight and variable hold of a control actuator such as actuators 22 and 24 such that an ideal position can be achieved by the clinician. By use of this variable resistance functionality the clinician can find the ideal position to do his procedure and increase the resistance to motion by further tightening the tensioning and thereby holding its set position. The resistance to movement functionality is achieved by three basic components: the friction cone 196 that is anchored to the handle 18; actuators 22 and/or 24 that have surfaces which match the angle of the friction cones and are free to turn as well as move slightly axially onto and off of the friction cone 196; and the cam 194 (or screw) that generates the side load and lateral motion of the actuators 22 and 24 onto the friction cones such as cone 196.

FIG. 26 provides an exemplary exterior view of the handle 18 including the tensioning knob 192 for applying a varying degree of resistance to movement of the actuators 22 and 24. Placing the tensioning knob 192 on a side of the handle 18 facilitates single-handed operation of the catheter assembly 10 via the exposed control surfaces of the actuators 22 and 24 and the tensioning knob 192. In alternative embodiments, the tensioning knob 192 comprises a slider external control surface that provides a variable amount of resistance to movement of the actuators 22 and 24 by moving the slider within a sliding range along the side of the housing 20 of the handle 18.

Figure 27:
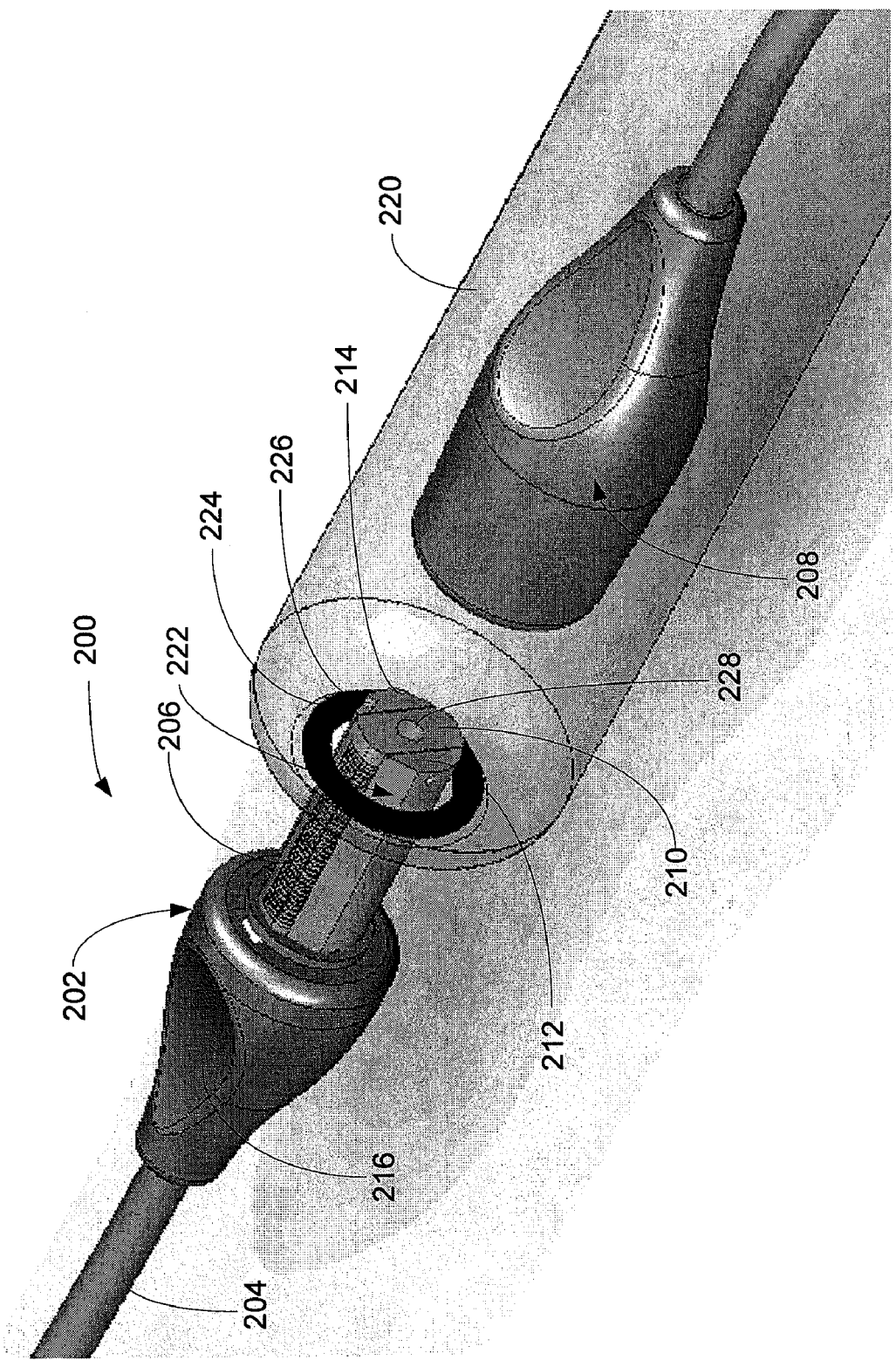
FIG. 27 is a view of a barrel connector for an ICE catheter depicted in a disconnected state.

Having described a detailed example of a device suitable for using a multi-wire barrel connector, attention is directed to FIG. 27 wherein an exemplary barrel connector 200 is illustratively depicted. In the illustrative example, a male connector component 202 is permanently coupled to a single-use ICE catheter assembly described herein above. In the illustrative example the male connector component 202 is connected via a cable 204 to the ICE catheter assembly. In an alternative embodiment the male connector component 202 is housed within the ICE catheter assembly handle.

In the illustrative example, the male connector component 202 includes at least a first flexible circuit 206 comprising a flexible substrate and a set of conductive lead lines deposited thereon. The lead lines have electrical contacts on an exposed surface of the cylindrically shaped male connector component 202 depicted in FIG. 27. By way of example, the first flexible circuit 206 comprises a set of 32 signal lines corresponding to 32 ultrasound transducer elements on the ICE catheter assembly. A second flexible circuit (not shown in FIG. 27), including a set of 32 signal lines having exposed contacts on a portion of the cylindrical surface opposing the exposed contacts of the first flexible circuit 206, is provided in the illustrative example to support a 64 element ICE catheter assembly. The flexible substrate is, by way of example, made of a polyimide having a thickness of 125 microns. The lead lines are made of gold, having a thickness of 75 microns. A manufacturer/provider of such flexible circuits is Dynamic Research Corporation (DRC Metrigraphics Division), 50 Concorde St., Wilmington, Mass.

In the illustrative example, the male connector component 202 comprises a set of three separate piece parts that fit together to form a cylindrical shape that engages a female connector component 208. The three separate pieces comprise: a flex circuit support 210 to which the first flexible circuit 206 and the second flexible circuit are conformed, a first flexible circuit clamp 212 and a second flexible circuit clamp 214. The flex circuit support 210, comprising a rigid plastic, defines a portion of the cylindrical shaped surface containing the contacts for the male connector component 202's signal lines. The flexible circuit clamps 212 and 214 locate and hold the flexible circuit 206 in position within a space between the clamps 212 and 214 and the interposed flex circuit support 210.

In the illustrative example, the 64 exposed contacts of the male component engage the corresponding ones of the 64 wire fingers of the female component when the male component is inserted into and then rotated only a small amount, less than a quarter turn, within the female component. In an exemplary embodiment, two separate guides are incorporated into the male and female connector components 202 and 208 to ensure proper engagement of male component flex circuit contacts and corresponding ones of the wire fingers when the male connector component 202 is inserted into and then rotated within the female connector component 208.

In a first instance, proper alignment of the male component 202's contacts and the female component 208's wire fingers is facilitated, in an illustrative embodiment, by a combination of a guide peg 240 (not shown in FIG. 27, but see FIG. 28a) and a corresponding channel/slot 226. The peg 240 matches a side opening in the corresponding channel/slot 226 depicted in FIG. 27. When the male component 202 is initially inserted, the channel/slot 226 guides the peg 240 to ensure that the wire fingers of the female component 208 are not damaged during insertion. When the male component 202 has been inserted to a proper depth in the female component 208, a second portion 226c of the channel/slot 226, running along an arc of the cylindrical outer surface of the male component 202, guides the peg 240 to ensure the contacts and the wire fingers are properly aligned as the male and female components 202 and 208 are rotated toward a fully engaged position. Thus the channel/slot 226 (illustrated better in FIG. 28b) receives the complimentary peg 240 extending inwardly within a cylindrical cavity of the female connector component 208. The channel/slot 226 guides the peg 240 as the male connector component 202 and the female connector component 208 slidably engage.

In a second instance, to further aid proper alignment between the male connector component 202 and the female connector component 208, in the exemplary embodiment a guide pin extends from a bottom of the female connector component 208's cylindrical cavity. The guide pin enters an axial shaft 228 within the male connector component 202. The guide pin operates as a pivot point during rotation of the male component 202 and female component 208 to affect an electrically conductive connection between the contacts of the flexible circuit 206 and corresponding wire fingers of the female connector component 208.

A connector body 216 holds the three pieces and flexible circuit of the male connector component 202. In an illustrative embodiment the connector body 216 includes at least one pre-formed indentation 218 facilitating easy gripping of the male connector component 202 when engaging the female connector component 208. The connector body 216 is suitably formed to receive, locate and hold the flex circuit support 210 and the flex circuit clamps 212 and 214. The connector body 216 also provides a suitable housing for signal line connections between the flexible circuit 206 and the cable 204. The female connector component is described further herein below with reference to FIG. 28a.

In the illustrative example, a sterile barrier is maintained between the male connector component 202 and the female connector component 208 by a sterile bag 220. The sterile bag 220 substantially encases the female component 208. An opening 222 includes a gasket 224 made of compressible foam rubber. The gasket 224 is sized to compressibly fit and seal a space between the male connector component 202 and the female connector component 208 when these components are fully engaged.

Figure 28A:
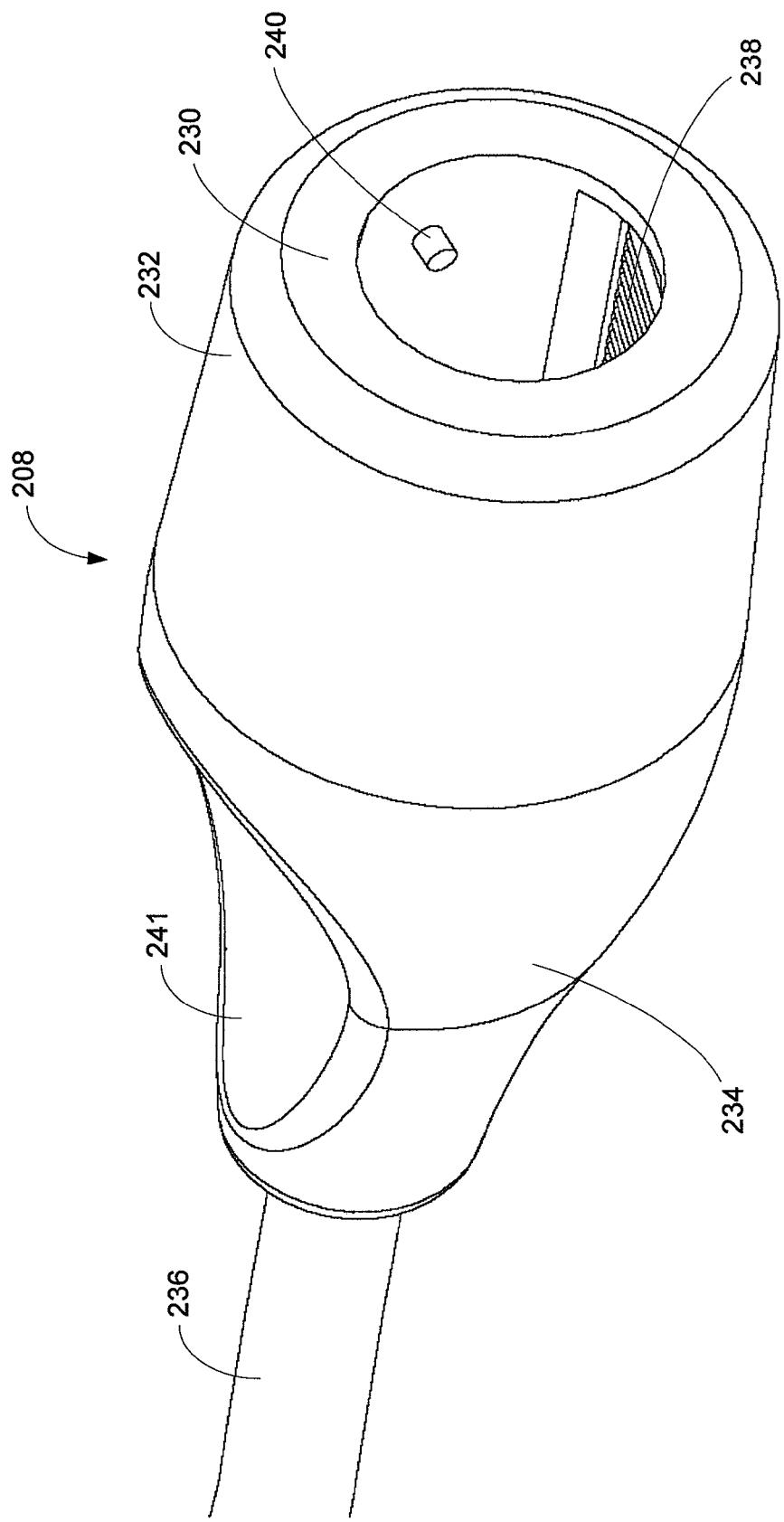
FIG. 28a is a view of a barrel portion of the connector depicted in FIG. 27.

Turning to FIG. 28a, an exemplary female connector component 208 is illustratively depicted. The female connector component 208 comprises three primary sub-components: a contact locator 230, a contact cover 232, and a connector body 234 including an opening through which a console cable 236 passes. The console cable 236, by way of example, comprises 64 signal lines that terminate at corresponding wire fingers within the female connector component 208.

The contact locator 230 includes an open-ended cylindrical cavity within which the male connector component 202 is inserted to affect connections between the flexible circuit 206 contacts and the corresponding wire fingers of the female connector component 208. The contact locator 230 includes at least a first set of 32 wire fingers 238 arranged to engage a corresponding set of 32 contacts of the male connector component 202's flexible circuit 206 when the male component 202 and the female component 208 are properly engaged. The wire fingers 238 are made, for example, from copper wires of sufficient strength to spring back and apply sufficient force against corresponding contacts of the flexible circuit 206 when the connector components 206 and 208 are fully engaged. The contact locator 230 also includes the peg 240 that is guided within a complimentary channel/slot 226 of the male connector component 202 (described herein with reference to FIGS. 27 and 28b). A guide pin located at the base of the cylindrical cavity defined by the contact locator 230 constrains the transverse movement of the male connector component 202 during engagement with the female connector component 208.

The contact cover 232 encompasses the contact locator 230 and prevents fluid access to the wire fingers 238 and other sensitive components of the female connector component 208. The contact cover 232 is made from, for example polycarbonate.

A connector body 234 provides a reference for mounting the contact locator 230 and contact cover 232 of the female connector component 208. In an illustrative embodiment the connector body 234 includes at least one pre-formed indentation 241 facilitating easy gripping of the female connector component 208 when engaging the male connector component 202. The connector body 234 includes a central shaft (not shown) for receiving the cable 236. The wires emerging from the central cable are attached to corresponding ones of the wire fingers 238.

Figure 28B:
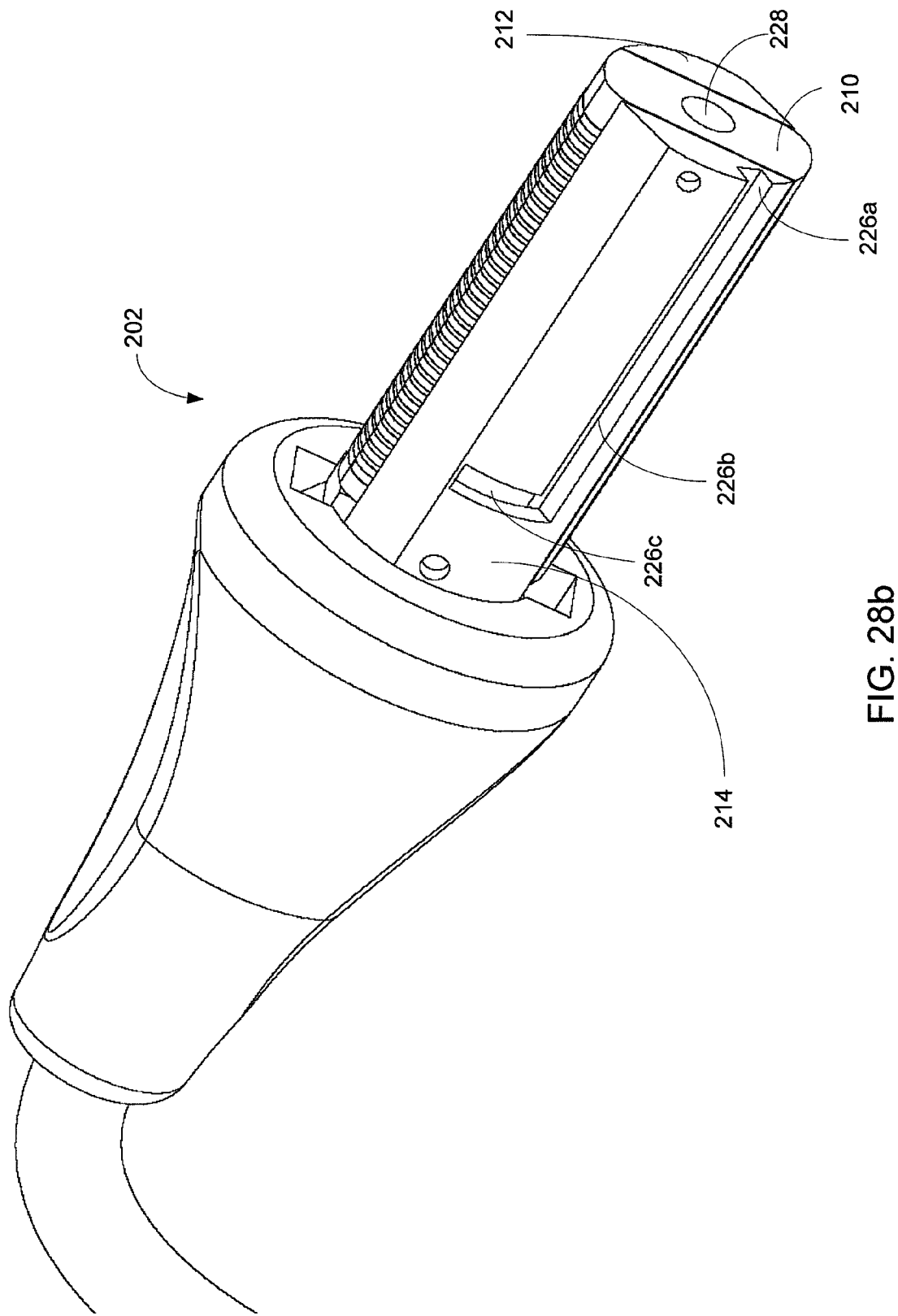
FIG. 28b is a view of a cylinder portion of the connector depicted in FIG. 27 rotated to show a guiding slot.

Turning briefly to FIG. 28b, the male connector component 202 (described herein above with reference to FIG. 27a) is shown from another perspective to depict the channel/slot 226. The channel/slot 226 cooperatively operates with the peg 240 to ensure proper alignment of the male component's contacts and the female component's wire fingers. The peg 240 of the female connector component 208 (see, FIG. 28a) matches a side opening 226a in the corresponding channel/slot 226. When the male component 202 is initially inserted, a first portion 226b, running lengthwise along the channel/slot 226, guides the peg 240 to ensure that the wire fingers 238 of the female component 208 are not damaged during insertion. When the male component 202 has been inserted to a proper depth in the female component 208, a second portion 226c of the channel/slot 226, running along an arc of the cylindrical outer surface of the male component 202, guides the peg 240 to ensure the contacts and the wire fingers are properly aligned as the male component 202 and female component 208 are rotated toward a fully engaged position. Thus the channel/slot 226 receives the complimentary peg 240 extending inwardly within a cylindrical cavity of the female connector component 208. The channel/slot 226 guides the peg 240 as the male connector component 202 and the female connector component 208 slidably and rotationally engage.

Figure 29:
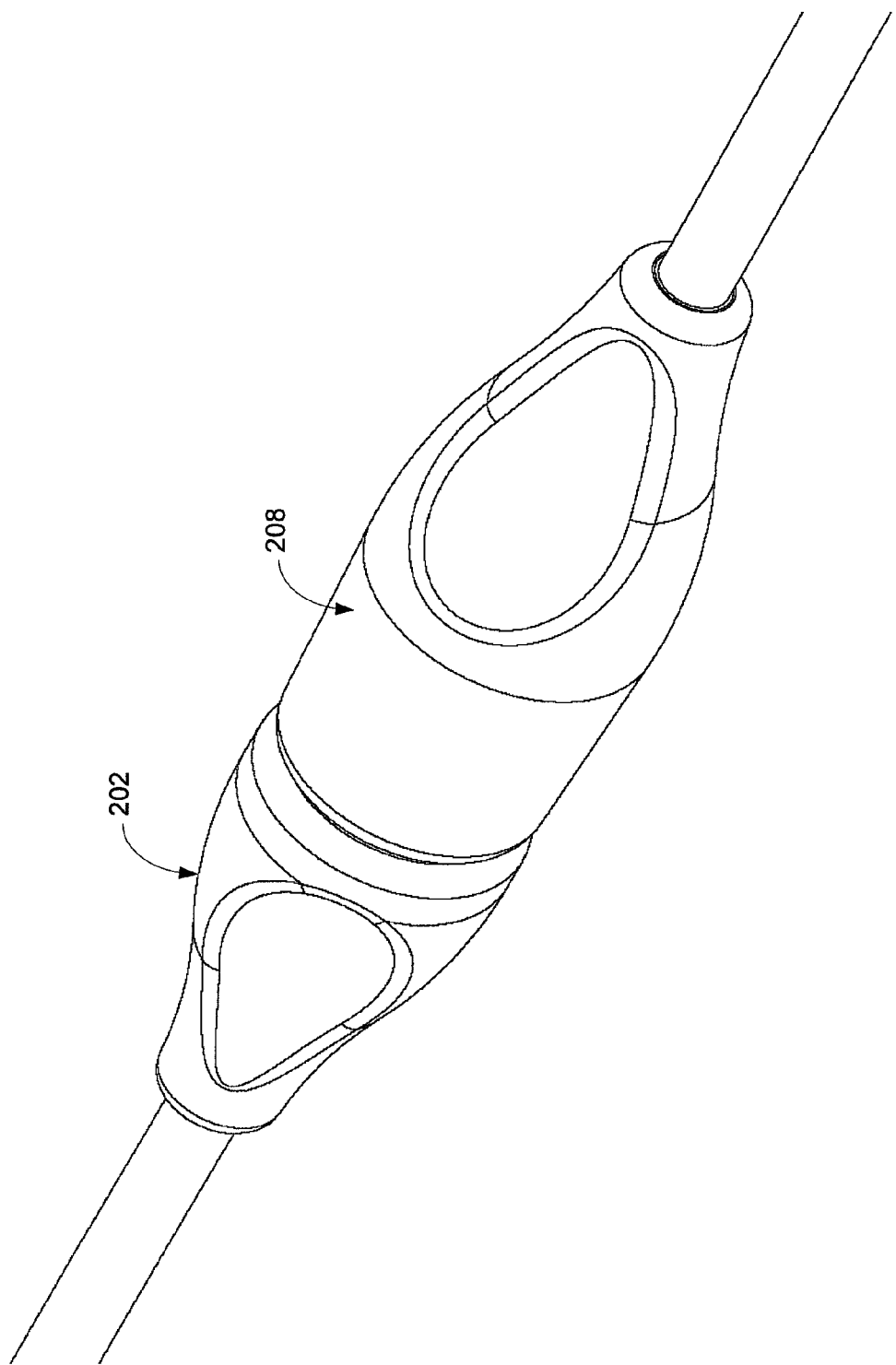
FIG. 29 is a view of the barrel connector for an ICE catheter depicted in a connected state.

Turning briefly to FIG. 29, the male connector component 202 and the female connector component 208 are depicted in their fully engaged arrangement. The sterile bag 220 and gasket 224 are not depicted in this view. The illustratively depicted connector assembly is relatively small in size. For example, in an exemplary embodiment the connector assembly for a 64 element ICE catheter assembly has a diameter of approximately 30 mm and an overall connect assembly length of 100 mm. The portion comprising the male connectors' wires is approximately 40 mm.

Figure 30:
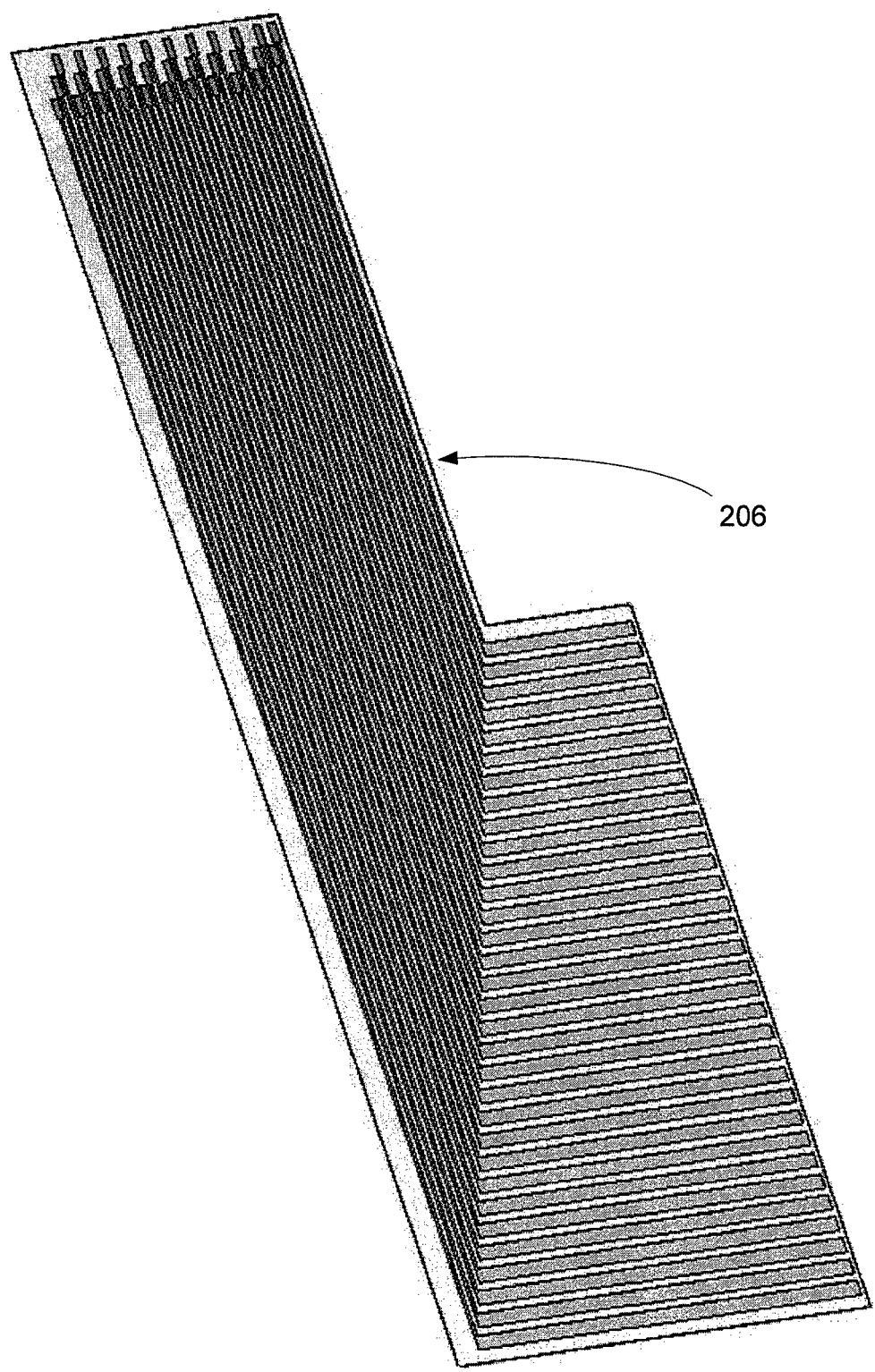
FIG. 30 depicts an exemplary flexible circuit component of the cylinder portion in a flat state.
Figure 31:
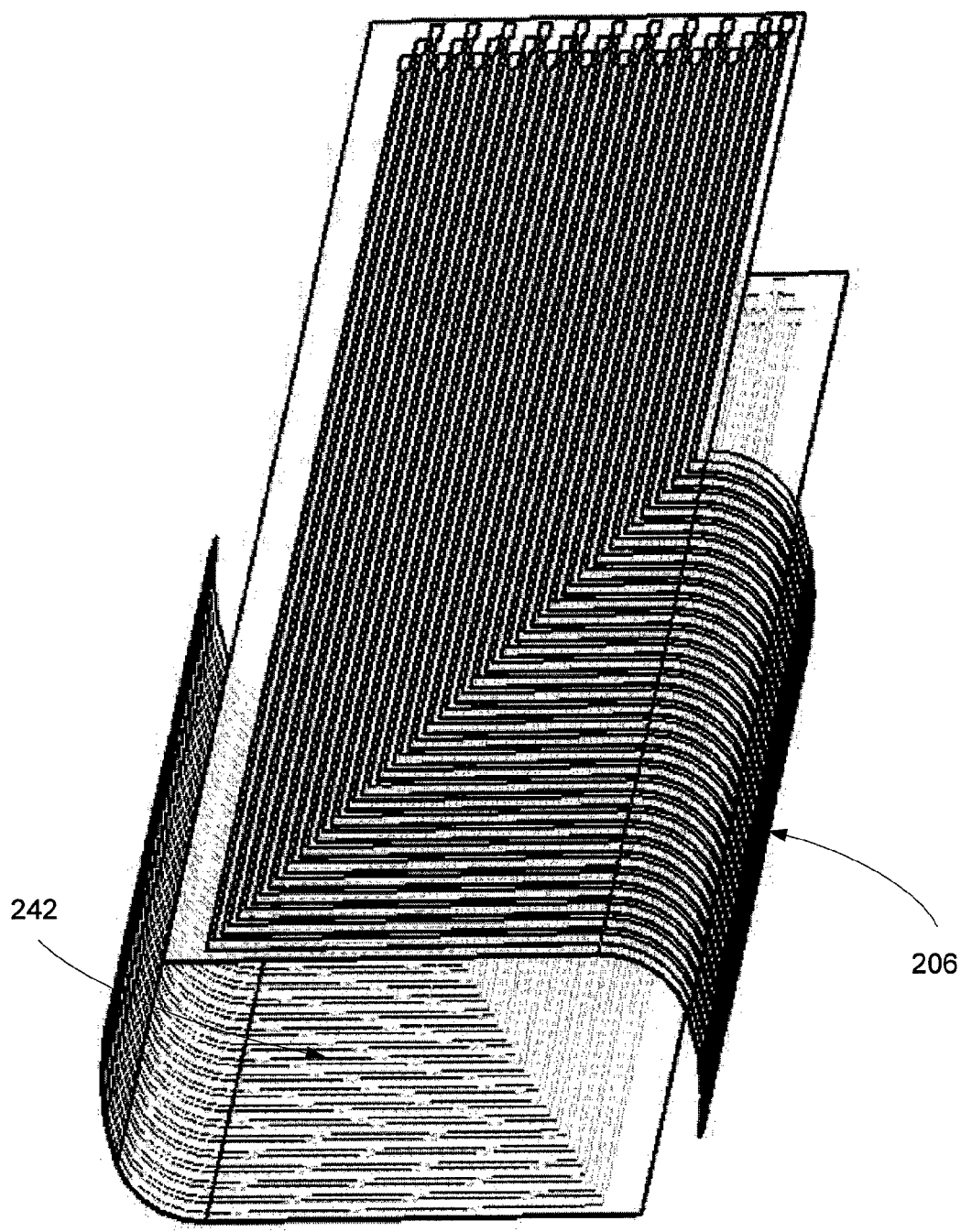
FIG. 31 depicts a pair of flexible circuits in their wrapped configuration in the cylinder portion depicted in FIG. 27 and FIG. 28b.

Turning briefly to FIGS. 30 and 31, the flex circuit 206 is depicted in a flat state and in a 3-dimensional representation corresponding substantially to the re-shaped arrangement when affixed to the flex circuit support 210 (see, FIG. 27). The drawing presented in FIG. 31 depicts a second flexible circuit 242 that was hidden in the view provided in FIG. 27 by the flex circuit support 210. The two flex circuits, when combined, support a 64 transducer array. Also, while not shown in FIGS. 30 and 31, at least a signal ground line is provided for the transducer elements via the connector 200.

Figure 32:
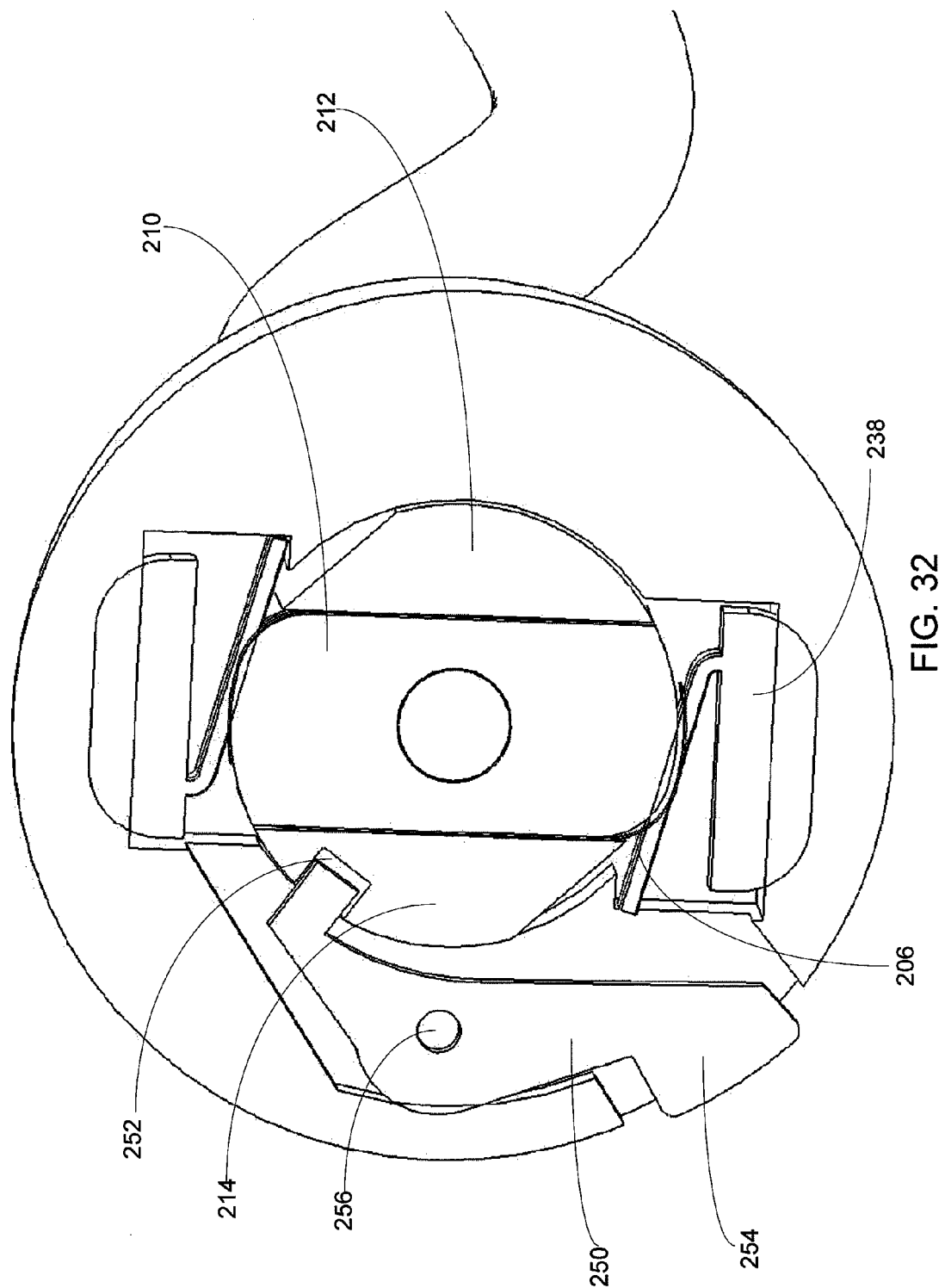
FIG. 32 is a cross-sectional view of the barrel connector of FIG. 27 depicting an exemplary locking mechanism for rotationally locking a barrel connector's cylinder and barrel portions once fully engaged.

Turning to FIG. 32, a schematic diagram is provided of an exemplary locking mechanism incorporated into the female connector component 208 to ensure that the contact and wire finger connections are maintained after initially inserting and rotating the male connector component 202 in the female connector component 208. In the exemplary embodiment, a rotation lock 250 is shown in an engaged position with a notch 252 within the flex circuit clamp 214. By way of example, the notch 252 is formed from the channel/slot 226.

In an exemplary embodiment, the rotation lock 250 snaps into a locking position within the notch 252 when the male connector component 202 has been sufficiently rotated within the female connector component 208 to create an electrical connection between the contacts of the flex circuit 206 and the wire fingers 238. Thereafter, the rotation lock 250 is held in the depicted locking engagement position by a tensioning spring (not shown) or other resistive force. The rotation lock 250 is released from its locking engagement by pressing an exposed release lever 254 on the rotation lock 250 causing rotation of the lock 250 about an axis 256.

Figure 33:
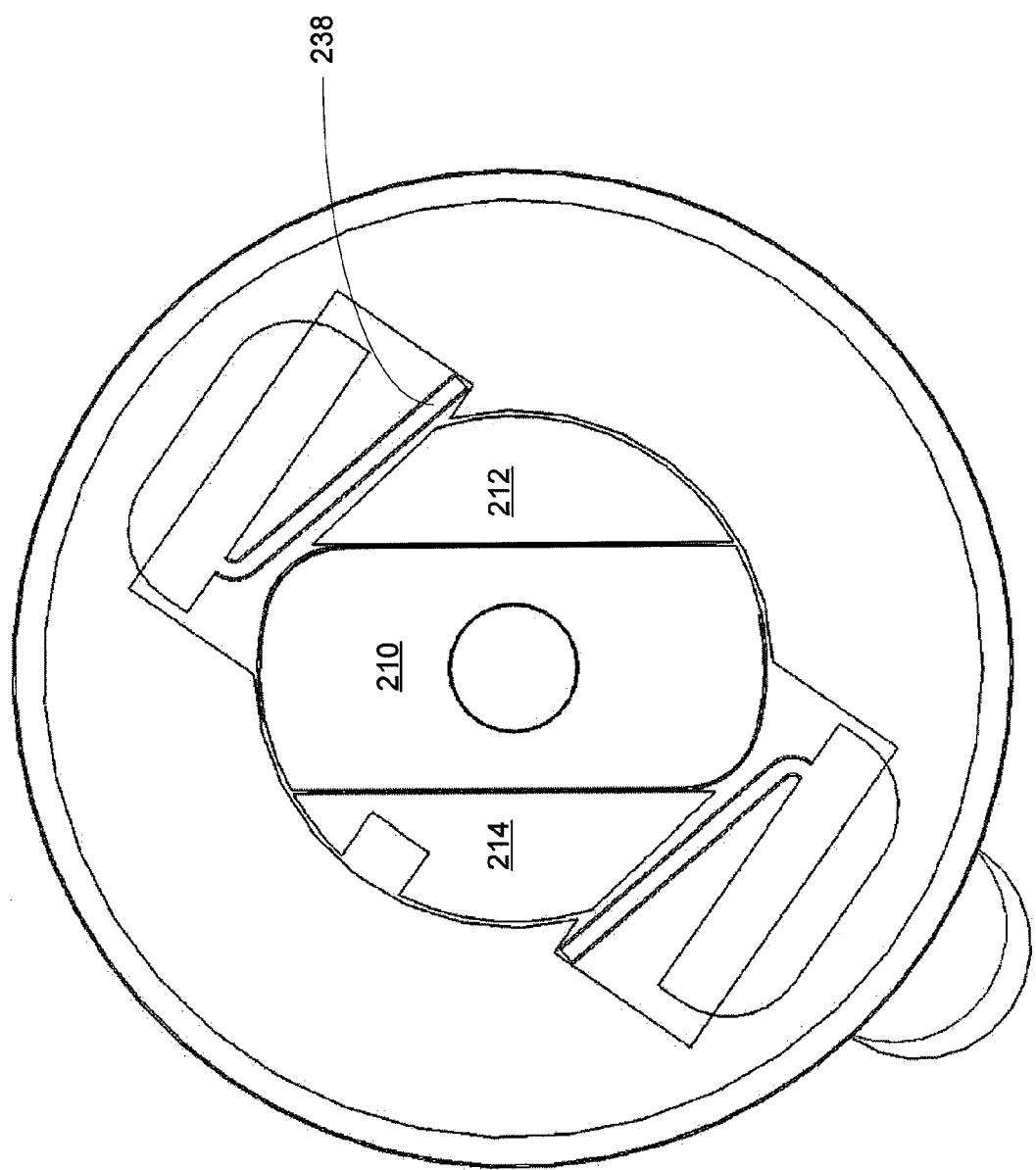
FIG. 33 is a cross-sectional view of the barrel connector of FIG. 27 depicting the barrel connector in a state of partial engagement wherein barrel and cylinder portions are depicted at a relative rotational state facilitating sliding engagement of the cylinder and barrel portions without damaging electrical connection leads.

FIG. 33 shows a cross-sectional view of the semi-mated male connector component 202 and female connector component 208 while in the non-rotated position. This view shows the non-uniform radius of the cylinder-shaped male connector component 202, and more particularly, the clearance provided by the flex circuit clamps 212 and 214 for the wire fingers 238 while the male component 202 and female component 208 are slidingly engaged (but not yet rotated into a fully engaged position depicted in FIG. 32). After the male connector is inserted to a proper depth in the female connector 208's cavity, the connectors 202 and 208 are rotated about an eighth of a turn to affect electrical signal coupling between the finger wires 238 and contacts of the flexible circuit 206.

The aforementioned non-uniform radius for the substantially cylindrical male connector component 202 is provided in a variety of structures and their resulting cross-section outlines. In the embodiment depicted in FIGS. 32 and 33, the non-uniform radius is provided by creating a flattened surface on a cylindrical male connector assembly's clamp components. In alternative embodiment the cross-sectional profile of the substantially cylindrical shaped male connector component exhibits a "cam" profile including a gradual cross-section radius change. Other non-uniform radius cross-sectional profiles for the male connector component, providing clearance for the wire fingers 238 when the male and female barrel connector components are initially engaged, are contemplated in alternative embodiments of the invention.

Figure 34:
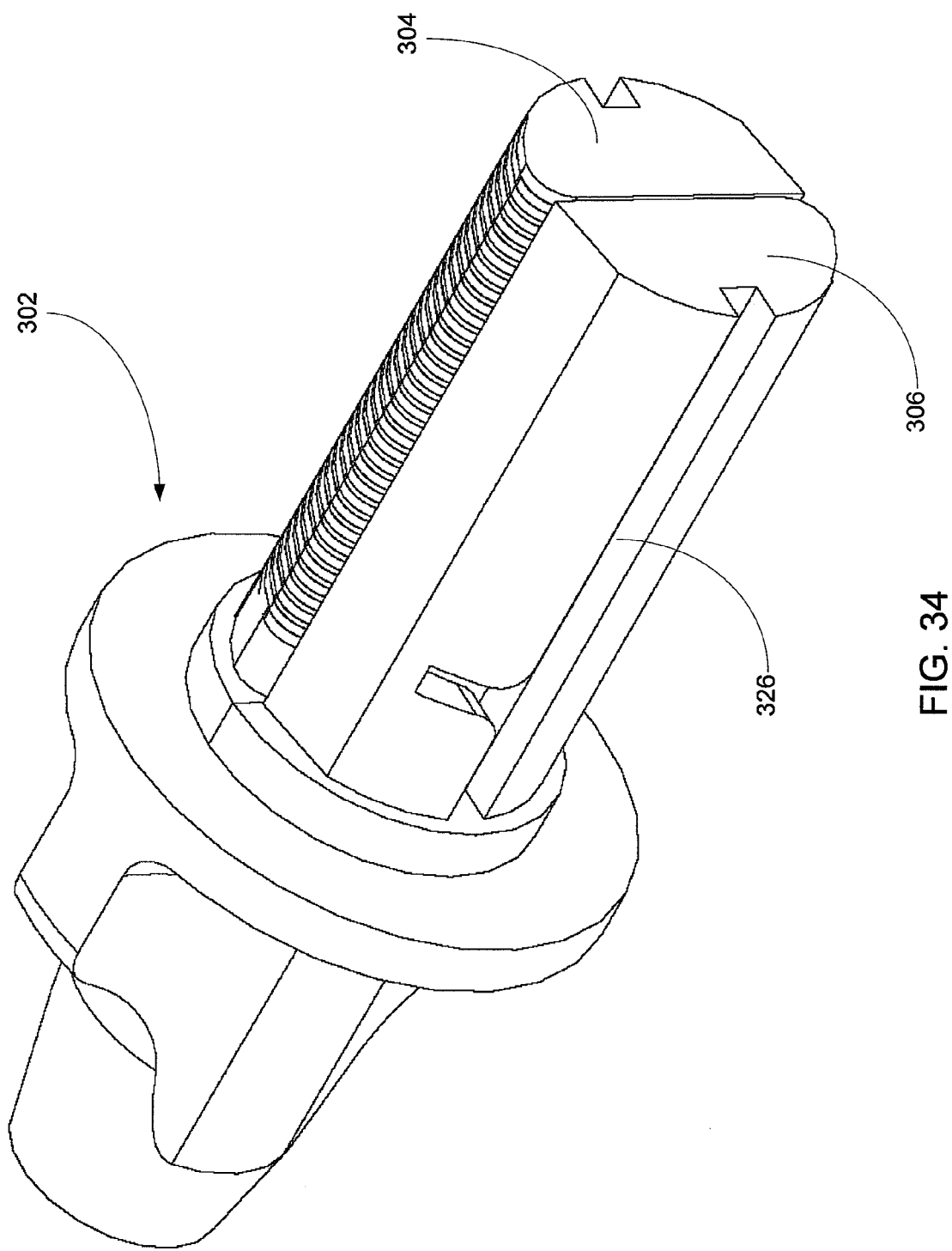
FIG. 34 is a view of a cylinder portion of an alternative embodiment of a barrel connector.
Figure 35:
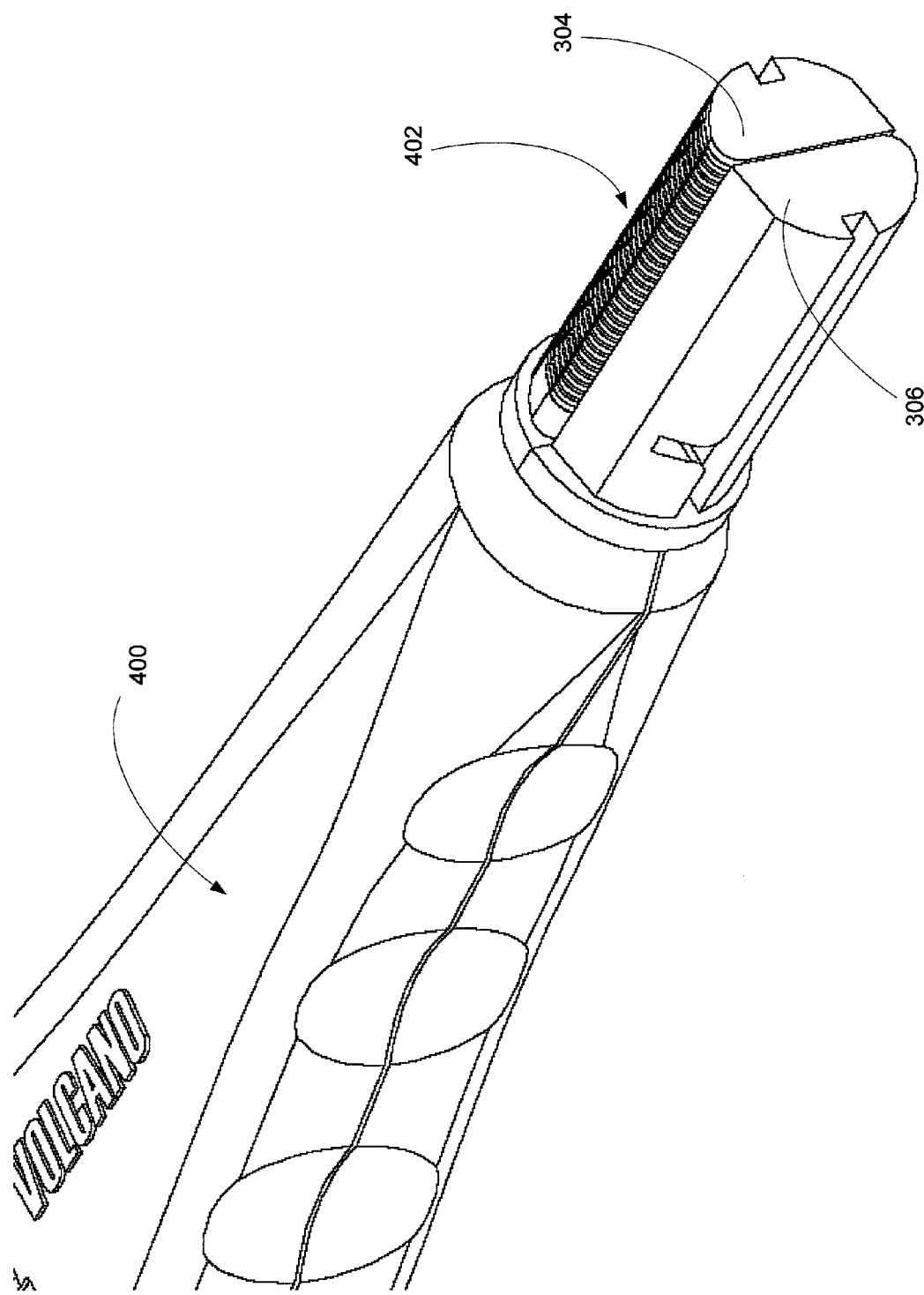
FIG. 35 is a view of an alternative embodiment of the cylinder portion depicted in FIG. 34 wherein the cylinder portion is incorporated directly into an ICE catheter handle.

The male connector component is potentially formed in a variety of ways. Turning briefly to FIG. 34, an alternative male connector component 302 is depicted wherein each one of two flexible circuit supports 304 and 306 carries a flexible circuit (e.g., flexible circuit 308). Furthermore, the flexible circuit support 306 depicts the channel/slot 326 corresponding to the channel/slot 226 in the embodiment depicted in FIG. 27. The flexible circuit support 306 also includes a notch 352 corresponding to the notch 252 in the embodiment depicted in FIG. 32. In yet another embodiment depicted in FIG. 35, a male connector component 402 is directly connected to a handle 400 of an ICE catheter assembly. Thus, it should be evident to those skilled in the art in view of the description of the following illustrative embodiments that there are a wide variety of structures that can be used to carry out the disclosed multi-wire barrel connector including multiple guides to ensure proper mating of the male and female connector components and prevent damage to fragile wires and leads.

It is also within the scope of the disclosed exemplary embodiments to incorporate the improvements described into other types of ultrasound catheters, such as for example IVUS catheters. RF backscatter based tissue characterization is used in IVUS to determine plaque type (fibrous, fibro-lipidic, calcified, necrotic, etc.). This type of analysis is also known as Virtual Histology. Using this imaging technique with myocardial tissue instead of atherosclerotic plaque, different types of myocardial tissue can be identified, including for example, healthy myocardium, dead myocardium, or diseased myocardium. Also, ablated and non-ablated tissue can be identified, such as the tissue in the pulmonary veins or other cardiac tissue. RF backscatter tissue characterization can also be used to more correctly identify the extent of calcification on diseased heart valves.

An alternative steerable catheter utilizes a backbone of two-way shape memory. Current is selectively sent through different sections of a two-way shape memory metal lattice structure, causing phase change due to differential heating. For example, when current is sent through nodes on one side, the distal segment 14 of the catheter shaft 12 bends in a first direction. When current is turned off in nodes on the first side and turned on in nodes on a second side, the tip bends in a second direction, different from the first.

Another alternative steerable catheter utilizes magnetic rings. The catheter has one or more magnetic bands at the tip. When used in a laboratory equipped with a magnetic guidance system, such as that made by Stereotaxis, the distal segment 14 of the catheter shaft 12 can be made to flex in reaction to specific magnetic fields that are produced.

Another alternative steerable catheter utilizes a micromotor. Instead of the rotatable tip being rotated in one direction or the other by turning a knob manually in the handle, a motor in the handle 18 rotates the assembly by pushing either a clockwise or counter-clockwise button. Alternatively, a micromotor is embedded in the tip and when a button in the handle is pressed, the micromotor rotates the rotatable tip.

Another alternative steerable catheter tip utilizes micromachines. An articulation or microgearing system is constructed in the distal end of the catheter using nanotechnology micro parts.

Another alternative steerable catheter utilizes spinning top articulation. The distal end of the catheter shaft 12 has two opposing spiral grooves in the wall. A rotatable tip is attached to a push rod, not a torque member. The rotatable tip has two tabs, one that slidably fits into each of the grooves. When the rod is pushed, the rotatable tip rotates to the right. When the rod is pulled, the rotatable tip rotates to the left.

Another alternative steerable catheter utilizes spinning top articulation combined with piezo power. A piezoelectric material is used as a mount for a transducer array at the tip of the catheter shaft 12. By activating the mount with a voltage, the mount oscillates a few degrees (for example 10 degrees), causing the transducer array to sweep back and forth, creating a 3D image.

Another alternative steerable catheter utilizes a superelastic material. Inside the catheter shaft 12 is a shaped mandrel of superelastic material which has a sliding stiff tube over it. When the stiff tube is pulled back, the superelastic mandrel takes its curved shape. When the stiff tube is advanced, the superelastic mandrel is straightened, causing the shaft to straighten with it. The distal end of the superelastic shaped mandrel is, by way of example, flattened.

Another alternative steerable catheter utilizes a hydraulic column. A polymeric catheter shaft is pre-shaped. It contains a lumen that is filled with a material such as a mineral or vegetable oil that is nontoxic and can be sterilized. A pistoning mandrel is slidable within the lumen. At the tip of the mandrel is a sealing stopper made from, for example, a ruby or ceramic ball for ultra low friction. As the mandrel is slid distally, the ball sealably slides within the lumen, increasing the pressure of the oil within the lumen and causing a curved tube to straighten, as in a Bourdon tube. Pulling on the mandrel lowers the pressure and allows the tubing to return to its shaped configuration.

It is to be understood that the embodiments of the invention that have been described are merely illustrative of many potential applications of the disclosed device. Numerous modifications may be made to the improved ultrasound catheter that facilitates one-hand maneuvering of a steerable distal segment and tip of a catheter assembly without departing from the spirit and scope of the presently disclosed exemplary embodiments.

What is claimed is:

1. A multi-wire barrel connector for coupling a signal wire bundle from a controller console to a hand-operated catheter assembly, the barrel connector comprising:
   a female connector component having a cylindrical cavity, the female connector component comprising:
      a set of wire fingers disposed within the cylindrical cavity, the set of wire fingers providing points of termination for a set of signal lines;
      a guide peg disposed on a surface of the cylindrical cavity at a point proximate an opening of the cylindrical cavity;
   a male connector component having a substantially cylindrical shape having a non-uniform transverse cross-section radius, the male connector component comprising:
      a set of signal leads disposed along arcs of a cylindrical surface of the male connector component, the set of signal leads being disposed along a majority of a length of the male connector component;
   a slot defined within a surface of the male connector component, the slot being arranged to accept the guide peg and constrain the relative positions of the male connector component and female connector component during engagement, the slot comprising a first segment running lengthwise along the male connector and a second segment guiding rotational engagement between the set of wire fingers and the set of signal leads; and
   wherein rotational lock structures incorporated into the female and male connector components ensure full engagement between the male connector and female connector component is maintained after rotating the male connector and female connector components into a fully engaged relationship; and
   wherein the set of signal leads is provided by at least a second flex circuit, and wherein signal leads for the first and second flex circuits are disposed on opposite sides of the male connector component and wherein the male connector component comprises first and second semi-cylindrical subcomponents, and wherein the first flexible circuit and second flexible circuit are carried by respective ones of the first and second semi-cylindrical components.

2. The barrel connector of claim 1 wherein the male connector component comprises a flex circuit support, a first clamping component, and a second clamping component;
   wherein the set of signal leads of the first flexible circuit and the second flexible circuit are carried by the flex circuit support interposed between the first and second components.

3. The barrel connector of claim 1 wherein the wire fingers are connected to signal lines from a control console signal interface.

4. The barrel connector of claim 1 wherein a lengthwise gap between the female connector component and the male connector component arising from the non-uniform transverse cross-section radius of the male connector provides clearance for the wire fingers during sliding engagement between the male connector component and female connector component.

5. The barrel connector of claim 1 wherein the wire fingers are spring wires that flex to accommodate rotational engagement with the complementary set of lead lines of the male connector component.

6. The barrel connector of claim 1 wherein at least 32 physical signal lines are supported by the set of signal leads.

7. The barrel connector of claim 1 wherein at least 64 physical signal lines are supported by the set of signal leads.

8. The barrel connector of claim 1 wherein the connector has an outer diameter of approximately 30 mm.

9. The barrel connector of claim 1 wherein the connector has a length on the order of 10 cm.

10. The barrel connector of claim 1 wherein a portion of the connector having the set of signal leads is approximately 40 mm.

11. The barrel connector of claim 1 further comprising a sterile field bag.

12. The barrel connector of claim 11 wherein the sterile field bag comprises a gasket integrated with a plastic sheet, the gasket providing a pressure seal between the female connector component and the male connector component when the barrel connector is fully engaged.

13. The barrel connector of claim 1 wherein the male connector component is integrated into a handle housing of a hand-operated controller for an intravascular imaging device.

14. The barrel connector of claim 13 wherein the intravascular imaging device is an intracardiac echocardiography device.

* * * * *